(12) United States Patent
Keilman et al.

(10) Patent No.: US 6,585,763 B1
(45) Date of Patent: Jul. 1, 2003

(54) IMPLANTABLE THERAPEUTIC DEVICE AND METHOD

(75) Inventors: George W. Keilman, Woodinville, WA (US); George E. Cimochowski, Dallas, PA (US)

(73) Assignee: VascuSense, Inc., Woodinville, WA (US)

(*) Notice: Subject to any disclaimer, the term of this patent is extended or adjusted under 35 U.S.C. 154(b) by 0 days.

(21) Appl. No.: 09/028,173

(22) Filed: Feb. 23, 1998

Related U.S. Application Data

(63) Continuation-in-part of application No. 08/949,413, filed on Oct. 14, 1997, now Pat. No. 5,807,258.

(51) Int. Cl.[7] .................................................. A61F 2/06
(52) U.S. Cl. ................................ 623/1.42; 604/891.1
(58) Field of Search ........................... 623/1.1, 1.42, 623/1.43; 604/891.1

(56) References Cited

U.S. PATENT DOCUMENTS

| | | | |
|---|---|---|---|
| 4,331,654 A | | 5/1982 | Morris |
| 4,391,281 A | | 7/1983 | Green |
| 4,484,569 A | | 11/1984 | Driller et al. |
| 4,558,690 A | | 12/1985 | Joyce |
| 4,652,257 A | | 3/1987 | Chang |
| 4,689,986 A | | 9/1987 | Carson et al. |
| 4,721,106 A | | 1/1988 | Kurtze et al. |
| 4,862,893 A | | 9/1989 | Martinelli |
| 5,016,615 A | | 5/1991 | Driller et al. |
| 5,113,859 A | * | 5/1992 | Funke ............................ 607/3 |
| 5,267,985 A | | 12/1993 | Shimada et al. |
| 5,423,334 A | * | 6/1995 | Jordan ..................... 623/912 X |
| 5,445,608 A | | 8/1995 | Chen et al. |
| 5,490,840 A | | 2/1996 | Uzgiris et al. |
| 5,524,624 A | | 6/1996 | Tepper et al. |
| 5,577,506 A | | 11/1996 | Dias |
| 5,656,015 A | | 8/1997 | Young |
| 5,694,936 A | | 12/1997 | Fujimoto et al. |
| 5,735,811 A | | 4/1998 | Brisken |
| 5,797,879 A | * | 8/1998 | DeCampli ..................... 604/96 |
| 5,807,258 A | | 9/1998 | Cimochowski et al. |
| 5,921,934 A | | 7/1999 | Teo |
| 5,957,844 A | | 9/1999 | Dekel et al. |
| 5,957,853 A | | 9/1999 | Giuffre |
| 5,967,986 A | | 10/1999 | Cimochowski et al. |
| 5,967,989 A | | 10/1999 | Cimochowski et al. |
| 6,132,419 A | * | 10/2000 | Hofmann ................. 604/890.1 |

FOREIGN PATENT DOCUMENTS

| | | | | |
|---|---|---|---|---|
| EP | 0 706 783 A1 | * | 4/1996 | ........ 623/FOR 100 |
| JP | 2-147073 A | * | 6/1990 | ........ 623/FOR 100 |
| RU | 2064784 C1 | * | 8/1996 | ........ 623/FOR 100 |

OTHER PUBLICATIONS

James W. Knutti and Henry V. Allen, "Integrated Circuit Implantable Telemetry Systems," *Engineering in Medicine and Biology Magazine*, pp. 47–50, Mar. 1983.

Shin–ichiro Umemura et al., "Sonochemical Activation of Hematoporphyrin: A Potential Modality for Cancer Treatment," *Ultrasonics Symposium*, pp. 955–960, 1989.

(List continued on next page.)

*Primary Examiner*—David H. Willse
(74) *Attorney, Agent, or Firm*—Davis Wright Tremaine LLP; Brian L. Johnson; George C. Rondeau, Jr.

(57) ABSTRACT

A system includes a first coil, a signal source and a first control module. The first control module regulates coupling between the signal source and the first coil. The system also includes an implantable device having a second coil coupled to a therapeutic transducer comprising an ultrasonic transducer. When the first coil is aligned with the second coil, the signal source is able to supply electrical power to the implantable device to enable the therapeutic transducer to operate. The control module is able to activate the therapeutic transducer under the control of a physician.

56 Claims, 12 Drawing Sheets

OTHER PUBLICATIONS

Clemens M. Zierhofer and Erwin S. Hochmair, "High–Efficiency Coupling–Insensitive Transcutaneous Power and Data Transmission Via an Inductive Link," *IEEE Transactions on Biomedical Engineerings* 37(7):716–722, Jul. 1990.

S. Umemura et al., "Sonodynamic Approach to Tumor Treatment," *Ultrasonics Symposium*, pp. 1231–1240, 1992.

R.J. Jeffers et al., "Enhanced Cytotoxicity of Dimethylformamide by Ultrasound In Vitro," *Ultrasonics Symposium*, pp. 1241–1244, 1992.

G.H. Harrison et al., "Effect of Ultrasonic Exposure Time and Burst Frequency on the Enhancement of Chemotherapy by Low–Level Ultrasound," *Ultrasonics Symposium*, pp. 1245–1248, 1992.

Mark C. Shults et al., "A Telemetry–Instrumentation System for Monitoring Multiple Subcutaneously Implanted Glucose Sensors," *IEEE Transactions on Biomedical Engineering* 41(10):937–942, Oct. 1994.

Jamille F. Hetke et al. "Silicon Ribbon Cables for Chronically Implantable Microelectrode Arrays," *IEEE Transactions on Biomedical Engineering* 41(4):314–321, Apr. 1994.

K. Fujimoto et al., "A New Cavitation Suppression Technique for Local Ablation Using High–Intensity Focused Ultrasound," *IEEE Ultrasonics Symposium*, pp. 1629–1632, 1995.

Shin–ichiro Umenura et al., "Effect of Second–Harmonic Phase on Producing Sonodynamic Tissue Damage," *IEEE Ultrasonics Symposium*, pp. 1313–1318, 1996.

Katsuro Tachibana and Shunro Tachibana, "Prototype Therapeutic Ultrasound Emitting Catheter for Accelerating Thrombolysis," *J. Jultrasound Med.* 16:529–535, 1997.

ImaRx Pharmaceutical Corp., "Technical Report: Drug and Gene Delivery," pp. 1–5, 14–16, and 18–19, Jul. 1997.

* cited by examiner

TO POWER SUPPLY
AND MONITORING
CONSOLE

IMPLANTABLE THERAPEUTIC DEVICE AND METHOD

CROSS-REFERENCE TO RELATED APPLICATION

This application is a continuation-in-part of application Ser. No. 08/949,413 filed Oct. 14, 1997, now issued as U.S. Pat. No. 5,807,258.

TECHNICAL FIELD

This invention relates generally to implantable devices, and, more particularly, to implantable medical devices having therapeutic or diagnostic functions and related methods.

BACKGROUND OF THE INVENTION

Diseased or defective portions of a patient's vascular system may be treated or replaced to correct or improve the patient's health. For example, persons requiring periodic hemodialysis to compensate for poor or absent renal function frequently are provided with arteriovenous grafts or shunts that couple a vein to an artery to facilitate coupling the patient to the dialysis unit. Dialysis, in turn, provides significant health benefits to the patient. In other cases, diseased portions of vasculature are replaced with or supplemented via grafts to facilitate blood flow or to reduce risk of rupture of an aneurysm. The grafts may comprise natural materials, e.g., a portion of a blood vessel taken from another area of the patient's body, or they may comprise artificial materials, such as DACRON™, TEFLON™or GORE-TEXT™ fabric. In still other cases, angioplasty is used to alleviate stenosis of major blood vessels. In all of these cases, narrowing of the vessel or graft lumen (stenosis or restenosis) is likely, whether from thromboses, deposited material or tissue growth within the treated area (endothelialization).

Following graft implantation, or surgery to relieve stenosis, it is difficult to monitor the condition of the affected area. Grafts and angioplastic surgery often fail after a period of time and for a variety of reasons. Several of the causal mechanisms are amenable to drug treatment. It is highly desirable in at least some of these cases to localize the drug treatment to the site of the graft or surgery. For example, when stenosis due to thrombosis threatens a given area, thrombolytic drugs are capable of providing significant assistance in resolving the thrombosis, but may present problems such as hemorrhaging, if they also act in other portions of the patient's body.

In other cases, steps may be taken to restore full fluid flow through, e.g., a graft that is becoming restricted, but only if treatment is initiated before the problem proceeds too far to be corrected without graft replacement. Since it is generally not possible to determine the condition of blood flow through a graft or vessel without invasive surgery to inspect it (or an angiogram), the procedure adopted with some grafts (e.g., access grafts for hemodialysis) is to replace the graft annually. Clearly, it would be preferable to be able to monitor the condition of a graft without resorting to invasive surgical procedures and without prescribing medication that may not be necessary, so that the useful life of the graft may be extended, problems associated graft failure avoided and so that medications are only prescribed when required by the known condition of the graft.

The best indicators of the condition of a graft are the velocity and volume of blood flowing through it. Fluid pressure at the distal and proximal ends of a graft (relative to the direction of blood flow) are a further indication of a graft's condition. As the lumen through a graft gradually becomes occluded with fatty buildup, other deposits or intima, the pressure differential across the graft increases, the velocity of blood in the lumen decreases and the flow of blood through the lumen decreases. Each of these parameters thus serves as an indication of the condition of the graft and its viability to support necessary blood flow.

Chen et al. propose a light generating system in U.S. Pat. No. 5,445,608. Among its drawbacks are that it requires a photosensitive drug that is activated via light from an implantable probe. A number of different embodiments are disclosed. In one of these, an array of light emitting diodes or solid state laser diodes are mounted on a light bar inside the implantable probe and are energized using either a storage battery power source, an inductively coupled external transformer, or with current provided in leads running through a flexible catheter that extends outside the patient's body to an external source.

SUMMARY OF THE INVENTION

According to principles of the present invention, a device and method are provided to achieve localized drug activation or localized drug delivery on an as-needed basis via an implanted therapeutic transducer that is coupled to an implanted electronic circuit. The implanted electronic circuit effects coupling of signals from a system external to a patient's body to the implanted electronic circuit via a magnetic coupling. The implanted therapeutic transducer may be activated via control signals transmitted from a control system that is external to the patient's body. Electrical power may be supplied to the implanted electronic circuit via the magnetic coupling, or, in some cases, via a hard-wired connection.

Optionally, a diagnostic transducer is also implanted that provides diagnostic information describing the condition of blood flow through a vascular graft to which the diagnostic transducer is coupled. This can allow a physician to determine that treatment is needed and then to activate the implanted therapeutic transducer to activate a drug in the vicinity of the vascular graft to which the therapeutic transducer is coupled.

In one embodiment, the therapeutic transducer comprises a cylindrical body including piezoelectric material wherein a first resonance frequency is determined by a thickness of the cylindrical body and a second resonance frequency is determined by a diameter of the cylindrical body. The cylindrical body includes a first electrode coupled to a first end of the cylindrical body and a second electrode coupled to a second end of the cylindrical body. An acoustic isolator may be disposed on the first electrode and on a sidewall of the cylindrical body. The acoustic isolator may comprise a mixture of microballoons and a polymer. The second electrode is coupled to a wall of the vascular graft. The first resonance frequency may be chosen to be related to the second resonance frequency by a factor of two.

In another embodiment, the present invention includes an ultrasonic transducer having a first surface, a sidewall and a second surface. A first electrode is disposed on the first surface. A second electrode is disposed on the second surface. An acoustic isolator having a low relative dielectric constant is disposed on the first surface and the sidewall. An acoustic reflector is maintained in alignment with and facing the second electrode of the ultrasonic transducer. In one embodiment, the acoustic reflector also functions as a permanent magnet or an electromagnet.

Further embodiments include transducers that provide magnetic, electromagnetic, optical, heat, ultrasonic or other kinds of signals for localized activation or delivery of drugs. These embodiments can allow a physician to provide needed therapy without requiring the trauma of surgery in order to maintain viability of a graft. This may also obviate graft replacement that is preventative in nature.

This invention provides an implantable diagnostic device for evaluating blood flow through vasculature on an ongoing basis that is capable of operating over an extended period of time. There is also provided an implantable therapeutic device for providing localized drug delivery or activation on an as-needed basis that is capable of operating over an extended period of time.

This invention provides the advantage that the physician can now locally activate or supply drugs in a variety of situations. For example, in situations where it is determined during surgery that part or all of a growth or tumor cannot be removed for safety or other reasons, the physician will be able to implant a therapeutic device, either on the growth or tumor or on the blood vessels supplying the growth or tumor with blood, to activate drugs directed to, or to selectively supply drugs to, the affected location or tissue. The therapeutic device may be able to be supplied with electrical power from time to time from a location outside the patient's body.

Yet another advantage that may be realized through practice of the present invention is the treatment of tumors or organs that are downstream of the blood vessel that includes a vascular graft that is coupled to a transducer. The transducer may be remotely activated to facilitate localized drug delivery or to provide other therapeutic benefits.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE INVENTION

When the status of fluid flow through a graft that has been implanted in a patient's vascular system is to be monitored for an extended period of time, or when an implanted system is used to deliver or activate drugs to an area near the implanted system over a long period of time or following implantation by an indeterminate interval, the implanted system used for this purpose will very likely need to receive energy from an external source and must convey signals to or from a monitoring device that is disposed outside the patient's body. In many cases, it may be desirable to deliver drugs to, or activate drugs delivered to, or monitor the status of flow through, multiple vessels or grafts or at multiple locations on a single vessel or graft. Thus, data signals to the implanted system to select transducers to trigger drug delivery or activation or indicating the status of fluid flow sensed by each separate transducer must be directed to each location of a selected transducer. However, in some cases, only a single transducer may be required to monitor a parameter such as flow or velocity, which is indicative of the internal condition of the graft, or to provide localized drug therapy or localized drug activation. The terms "implanted" and "implantable" are used herein to describe implanted or implantable devices that are intended to be permanently emplaced within a patient's body but that may be removed or replaced at a later date for a variety of reasons, and to distinguish these types of devices from devices, such as angioplasty catheters, stent delivery catheters and the like which are inserted into the body for relatively short periods of time.

Figure 1:
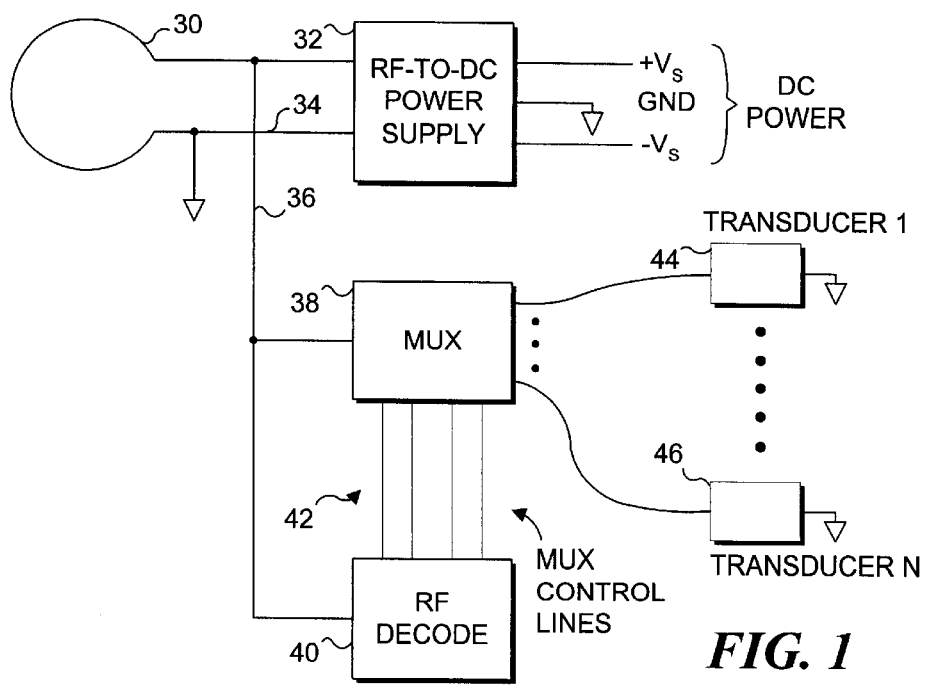
FIG. 1 is a block diagram showing a first embodiment, according to the invention, of an implantable electronic circuit for coupling electrical signals to or from a selected transducer of a plurality of transducers.

FIG. 1 illustrates a first embodiment of an implantable electronic circuit for localized drug delivery or activation or for monitoring flow, applicable to the situation in which n transducers 44–46 are included on one or more vessels or vessel grafts in the patient's body. Variations of the implantable electronic circuit shown in FIG. 1 are discussed below to accommodate specific conditions. In addition, other embodiments of implantable electronic circuits are illustrated in FIGS. 2 through 6. These embodiments, like that of FIG. 1, are useful for providing power to transducers that locally dispense or activate drugs or monitor fluid flow or velocity through a vessel, and for transmitting data signals from the transducers 44–46 to a monitoring console outside a patient's body. Some of these implantable electronic circuits are better suited for certain situations than others, and again, variations in the implantable electronic circuits are discussed below, as appropriate. Examples of implantable telemetry systems are discussed in *A Telemetry-Instrumentation System For Monitoring Multiple Subcutaneously Implanted Glucose Sensors* by M. C. Shults et al., IEEE Trans. Biomed. Eng., Vol. 41, No. 10, October 1994, pp. 937–942 and *Integrated Circuit Implantable Telemetry Systems* by J. W. Knutti et al., Eng. in Med. and Bio. Magazine, March 1983, pp. 47–50.

Each of the implantable electronic circuits shown in FIGS. 1 through 6 are intended to be implanted within the patient's body and left in place at least during the period in which therapy is necessary. Although separate functional blocks are illustrated for different components of the implantable electronic circuits in these Figures, any of the implantable electronic circuits can be implemented in one or more application specific integrated circuits (ASICs) to reduce size, which is particularly important when the implantable electronic circuits are integral with a graft. The implantable electronic circuits can be either included within the wall of a vessel, or in the wall of a graft in the case of a synthetic (i.e., man-made) graft, or may be simply affixed to or implanted adjacent to the graft for either natural vessels, man-made grafts or natural grafts that comprise a portion of a vessel taken from a different location in the patient's circulatory system. Additionally, the implantable electronic circuits may be coupled to a transducer 44–46 that is in turn coupled either to an organ or tumor or to a blood vessel that supplies blood to an organ or tumor where localized drug activation potentially provides therapeutic advantages.

Each of the implantable electronic circuits shown in FIGS. 1 through 6 includes a RF coupling coil 30, which is coupled via lines 34 and 36 to a RF-to-DC power supply 32. The RF-to-DC power supply 32 rectifies and filters a RF excitation signal supplied from an external source to the RF coupling coil 30, providing an appropriate voltage DC power signal for the other components of the implantable electronic circuits illustrated in these Figures. In the simplest case, the RF-to-DC power supply 32 would only require rectifiers and filters as appropriate to provide any needed positive and negative supply voltages, $+V_s$ and $-V_s$. However, it is also contemplated that the RF-to-DC power supply 32 may provide for a DC-to-DC conversion capability in the event that the electromagnetic signal coupled into the RF coupling coil 30 fails to provide the required DC voltage level for any component. This conversion capability increases the lower voltage produced by the direct coupling of the external RF excitation signal received by the RF coupling coil 30, to a higher DC voltage. Details of the RF-to-DC power supply 32 are not shown, since such devices are conventional. It is also contemplated that it may be necessary to limit the maximum amplitude of the RF input signal to the RF-to-DC power supply 32 to protect it or so that excessive DC supply voltages are not provided to the other components. Alternatively, each component that must be provided with a limited DC voltage supply may include a voltage limiting component, such as a zener diode or voltage regulator (neither shown). In another embodiment, the RF coupling coil 30 and the RF-to-DC power supply 32 of FIGS. 1 through 6 may be replaced by a hard-wired connection to supply DC or AC power in applications where the implant is needed for a relatively short duration where the inconvenience of the cables supplying the power is tolerable and the risk of infection is manageable. An example of a hard-wired transcutaneous connection for chronic implants is described in *Silicon Ribbon Cables For Chronically Implantable Microelectrode Arrays* by J. F. Hetke et al., IEEE Trans. Biomed. Eng., Vol. 41, No. 4, April 1994, pp. 314–321.

The RF-to-DC power supply 32 may include a battery or a capacitor for storing energy so that the RF coupling coil 30 need not be energized by a power signal in order for the implantable electronic circuit to operate, or at least, should include sufficient storage capability for at least one cycle of receiving energy and operating to deliver or activate drugs, or for transmitting data indicative of graft or vessel status to locations outside the patient's body. Neither a battery nor power storage capacitor are illustrated in the Figures, since they are conventional also.

Implantable electronic systems using battery power may only require the ability to receive data and control signals and may include the ability to transmit signals. As a result, they do not necessarily require access to the skin, which facilitates efficient coupling of power signals. A battery-powered system may result in a very compact implanted system. Alternatively, a battery-powered system that also is capable of recharging the battery via power signals coupled through an implanted coil can permit continuing treatment or diagnosis without requiring that a physician be present throughout the treatment or requiring the patient to be in the medical facility.

Figure 2:
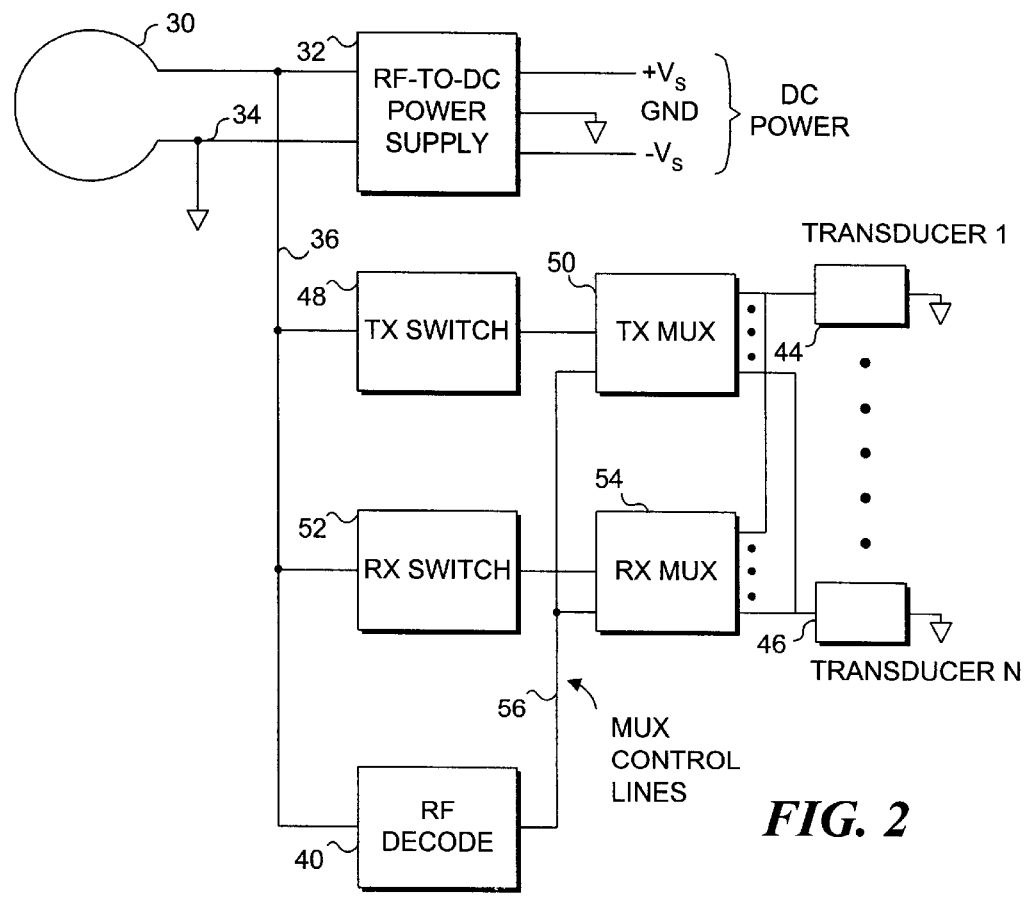
FIG. 2 is a block diagram of a second embodiment of an implantable electronic circuit for coupling electrical signals to or from a transducer using separate multiplexers for transmit and receive functions.
Figure 3:
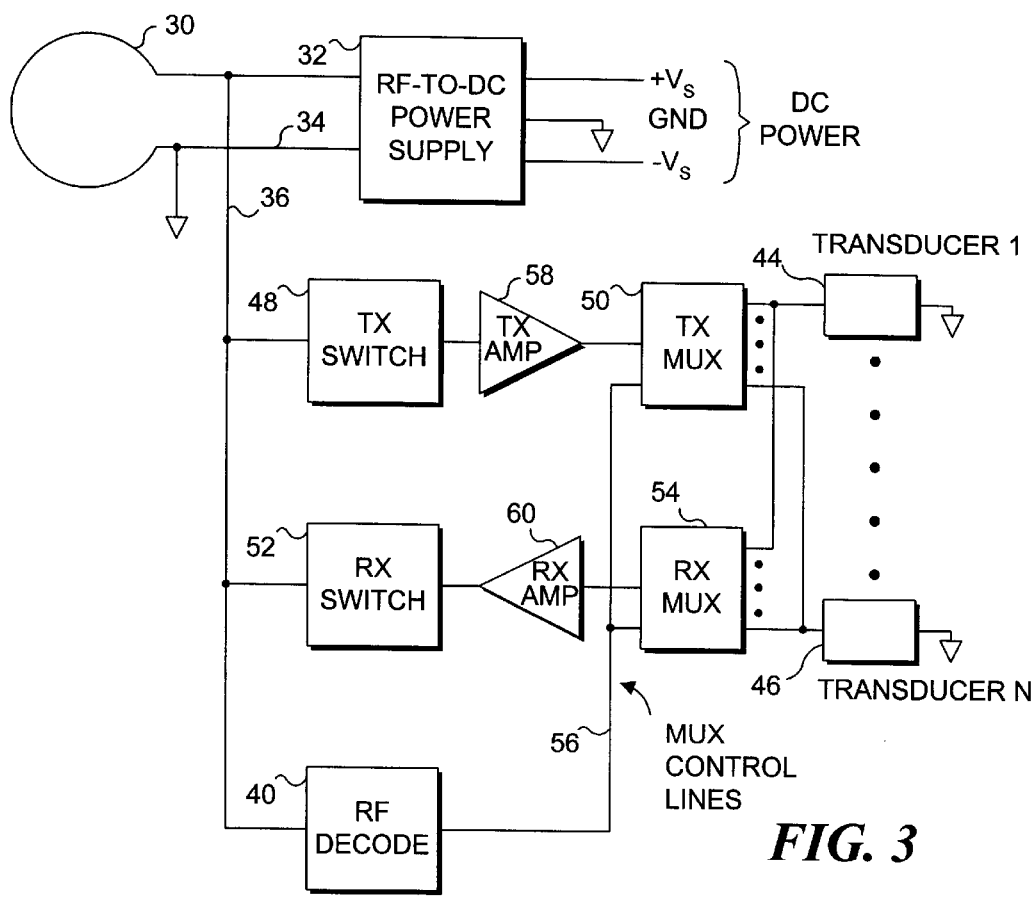
FIG. 3 is a block diagram of a third embodiment of an implantable electronic circuit for coupling electrical signals to or from a transducer using separate multiplexers and amplifiers for transmit and receive functions.

An element that is common to each of the circuits shown in FIGS. 1 through 3 is a RF decode section 40, which is used for generating control signals that are responsive to information encoded in the external RF excitation signal received by the RF coupling coil 30. This information can be superimposed on the RF excitation signal, e.g., by amplitude or frequency modulating the received signal. In some embodiments, including those where a battery is used, the RF decode section 40 may also include a RF oscillator for providing the RF signals to the transducers 44–46 or for coupling signals from the transducers 44–46 to external electronic apparatus.

In regard to the implantable electronic circuits shown in FIGS. 1 through 3, the RF excitation frequency is the same as the frequency used to provide energy for localized drug activation or for coupling of diagnostic signals. In one embodiment, the energy is used to excite a selected ultrasonic transducer 44–46 to produce an ultrasonic wave that propagates through a vessel graft, organ or tumor that is being treated, or a vessel supplying blood to an area that is being treated, or for conveying data from that transducer 44–46 receiving the ultrasonic waves. This approach generally simplifies the implantable electronic circuitry but may not provide optimal performance. Therefore, FIGS. 4 and 5 disclose implantable electronic circuitry in which the RF excitation frequency used to provide power to the RF-to-DC power supply 32 and to provide control signals to the RF decode section 40 is decoupled from the frequency that is used for exciting the transducers 44–46 and for modulating the data that they may provide in order to enable transmission to a point outside the patient's body.

Implantable Electronic Circuits

Referring now to FIG. 1, line 36 from the RF coupling coil 30 is coupled to a multiplexer (MUX) 38 to convey signals to or from a selected one of a plurality of n transducers 44–46 that are coupled to the MUX 38. In one embodiment, the RF decode section 40 provides a control signal to the MUX 38 through MUX control lines 42 to select that transducer 44–46 which will provide the data signal related to the status of flow through the graft being monitored. In another embodiment, the RF decode section 40 provides a control signal to the MUX 38 through MUX control lines 42 to select that transducer 44–46 which provides energy for localized drug activation. The control signal causes the MUX 38 to select the specific transducer 44–46 that is to be excited by the RF signal received by the RF coupling coil 30 and further causes the MUX 38 to select the transducer 44–46 that will be employed to deliver or activate drugs.

A variety of transducers 44–46 may be employed for diagnostic or therapeutic purposes. For example, in one embodiment the implantable electronic circuit shown in FIG. 1 can also be used in connection with pressure transducers. For ultrasonic transducers, the implantable electronic circuit is perhaps more applicable to the Doppler type for use in monitoring fluid velocity through a graft. If a single-vessel pulse Doppler transducer is used, the same transducer 44–46 can be used for both transmission and reception of the ultrasonic wave, thereby eliminating the need for the MUX 38. In the event that the transducers 44–46 shown in FIG. 1 are used for transit time flow measurements, it will normally be necessary to use the MUX 38 to switch between the transducer 44–46 used for transmitting the ultrasonic wave and that transducer 44–46 which is used to receive the ultrasonic wave.

For a single-vessel transit time measurement, a pair of opposed transducers 44–46 that are disposed on opposite sides of the graft are typically used. In order to acquire bidirectional fluid flow data, the direction of the ultrasound wave propagation must be known, i.e., the direction in which the ultrasound wave propagates relative to the direction of fluid flow through the vessel. In this case, the MUX 38 is required. However, for single-vessel applications in which the fluid flow is in a single known direction, the transducers 44–46 that are disposed on opposite sides of the graft can be electrically coupled in parallel or in series, eliminating any requirement for the MUX 38. The RF-to-DC power supply 32 and the RF decode section 40 could also then be eliminated, since the retarded and advanced transit time signals would be superimposed on the same RF waveform transmitted by the RF coupling coil 30 to locations outside the patient's body. Although this modification to the implantable electronic circuit shown in FIG. 1 would not permit the direction of fluid flow through a graft to be determined, the retarded and advanced transit time signals interfere over time, and this interference can be used to estimate the magnitude of fluid flow through the graft.

In some applications, a single transducer 44–46 or group of transducers 44–46 may be employed, in which case the implantable electronic circuit of FIG. 1 may be simplified by coupling the transducer(s) 44–46 directly to the RF coupling coil 30 and eliminating the MUX 38. In this embodiment, the RF decode section 40 and the RF-to-DC power supply 32 are optional; if the transducer 44–46, for example, requires DC excitation or other excitation different than that which may be provided directly via the RF coupling coil 30, inclusion of the RF-to-DC power supply 32 may be desirable. Similarly, some sensors may have more than one function and then the RF decode section 40 may also be desirable. Similarly, the implantable electronic circuits of FIGS. 2 through 6 may be modified to provide the desired or required functionality.

In FIG. 2, an implantable electronic circuit is shown that uses a transmit multiplexer (TX MUX) 50 and a receive multiplexer (RX MUX) 54. In addition, a transmit (TX) switch 48 and a receive (RX) switch 52 couple line 36 to the TX MUX 50 and RX MUX 54, respectively. The RF decode section 40 responds to instructions on the signal received from outside the patient's body by producing a corresponding MUX control signal that is conveyed to the TX MUX 50 and the RX MUX 54 over the MUX control lines 56 to select the desired transducers 44–46.

When selected transducers 44–46 are being activated, the TX switch 48 couples the RF excitation signal received by the RF coupling coil 30 to the activated transducer 44–46 that is selected by the TX MUX 50. The TX switch 48 allows excitation signals to pass to the selected transducer 44–46 only when the signals are above a predetermined voltage level, for example, 0.7 volts. Signals below that predetermined voltage level are blocked by the TX switch 48. Similarly, the RX switch 52 couples that transducer 44–46 selected by the RX MUX 54 to the RF coupling coil 30 and passes only signals that are below the predetermined voltage level, blocking signals above that level. Accordingly, the RF signal used to excite a first transducer 44–46 selected by the TX MUX 50 passes through the TX switch 48 and the lower amplitude signal produced by a second transducer 44–46 selected by the RX MUX 54 to detect a response to the ultrasonic signal transmitted through the graft is conveyed through the RX MUX 54 and the RX switch 52 and transmitted outside the patient's body through the RF coupling coil 30.

The implantable electronic circuit shown in FIG. 3 is similar to that of FIG. 2, but it includes a transmit amplifier (TX AMP) 58 interposed between the TX switch 48 and the TX MUX 50 and a receive amplifier (RX AMP) 60 interposed between the RX MUX 54 and the RX switch 52. The TX AMP 58 amplifies the excitation signal applied to the transducer 44–46 selected by the TX MUX 50 for producing the ultrasonic wave that is propagated through a graft or vessel. Similarly, the RX AMP 60 amplifies the signal produced by the transducer 44–46 selected by the RX MUX 54 before providing the signal to the RX switch 52 for transmission to locations outside the patient's body. Again, the circuit shown in FIG. 3 is most applicable to transit time flow measurements and employs the same frequency for both the RF excitation signal that supplies power to the RF-to-DC power supply 32 and the signal applied to a selected one of the transducers 44–46 to generate the ultrasonic wave propagating through the graft or vessel.

Figure 4:
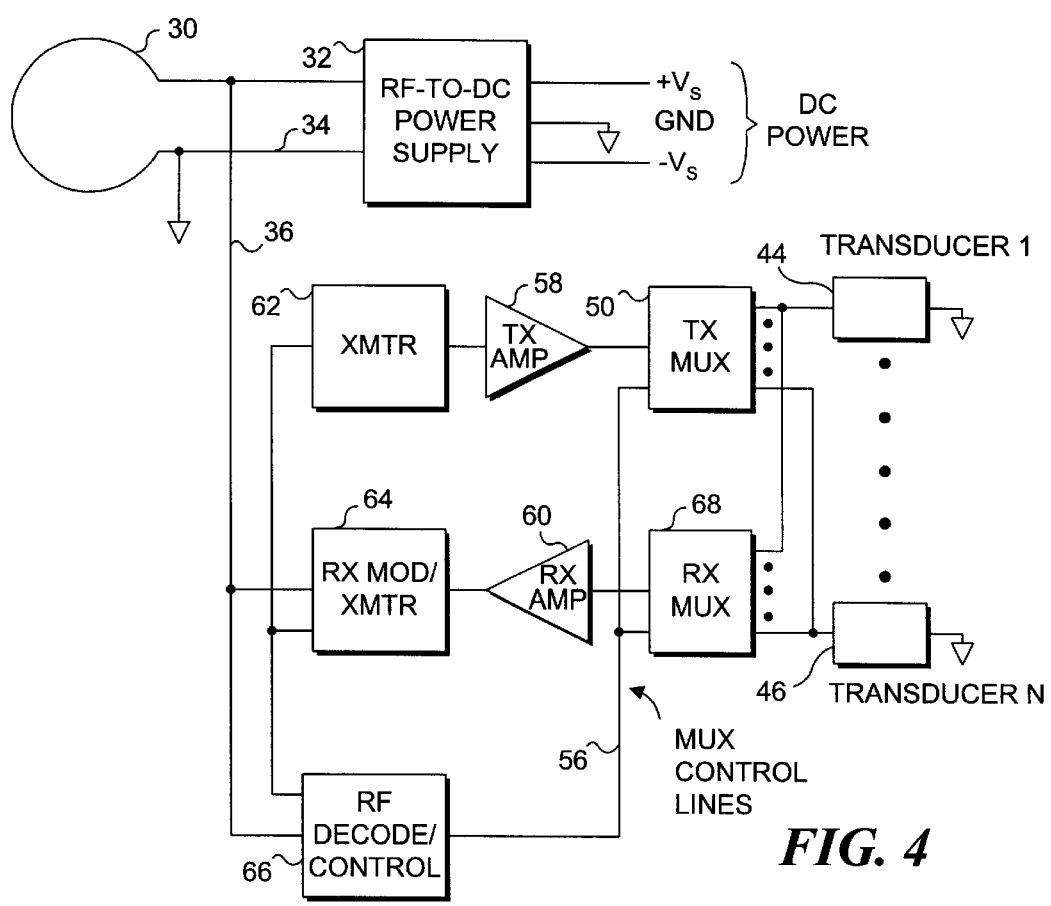
FIG. 4 is a block diagram of a fourth embodiment of an implantable electronic circuit for coupling electrical signals to or from a transducer that employs a local transmitter to excite a selected transducer, and a modulator/transmitter for transmitting signals from the transducers.
Figure 5:
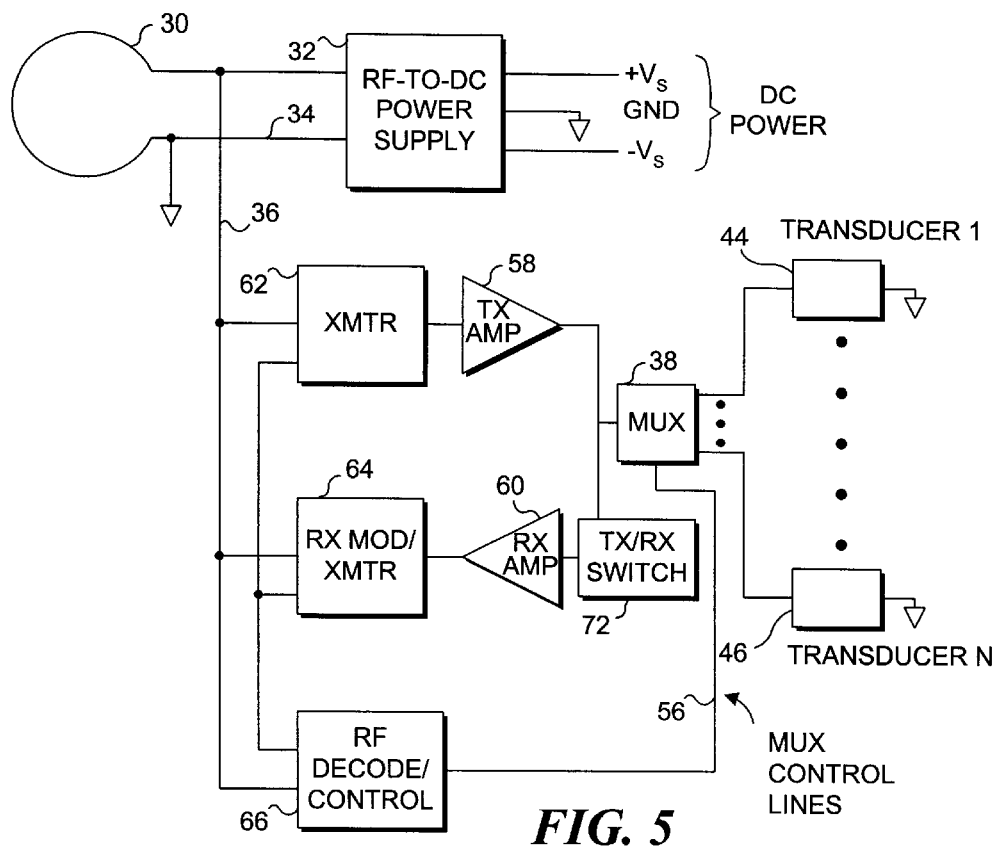
FIG. 5 is a block diagram of a fifth embodiment of an implantable electronic circuit for coupling electrical signals to or from a transducer, where one transducer is selected for transmitting and receiving, and a modulator/transmitter is used for transmitting the signal produced by the receiving transducer.
Figure 6:
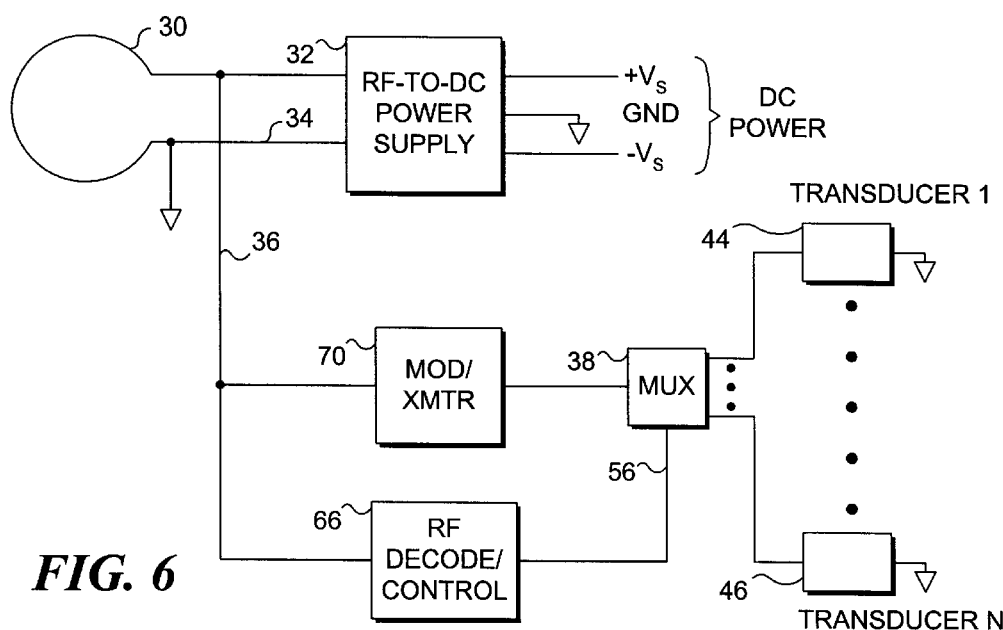
FIG. 6 is a block diagram of a sixth embodiment of an implantable electronic circuit for monitoring the status of a graft, wherein one of a plurality of transducers is selectively coupled to a modulator/transmitter or a receiver.

In contrast to the implantable electronic circuits shown in FIGS. 1 through 3, the implantable electronic circuits shown in FIGS. 4 through 6 enable the RF excitation frequency applied to the RF-to-DC power supply 32 to be decoupled from the frequency of the signal applied to excite any selected one of the transducers 44–46. Similarly, the signal produced by the transducer 44–46 receiving the ultrasonic waves propagating through the graft or vessel may be at a different frequency than the RF excitation frequency. In FIGS. 4 and 5, a transmitter (XMTR) 62 and a receive modulator/transmitter (RX MOD/XMTR) 64 are coupled to and controlled by a RF decode/control section 66. The RF decode/control section 66 determines when the excitation frequency is generated for application to a selected transmit transducer 44–46. The RF decode/control section 66 also determines when the signal produced by the transducer 44–46 selected to receive the ultrasonic wave is used for modulating the RF signal applied to the RF coupling coil 30. An advantage of this approach is that the RF power delivered to the RF coupling coil 30 may be chosen to be at an optimal frequency for penetration through the patient's body, thereby improving the efficacy with which the RF energy couples to a specific depth and location within the body. Another reason is for satisfying any requirements for selecting a particular frequency to comply with radio frequency allocation bands for medical equipment. Similarly, the frequency applied to any selected transducers 44 and 46 to stimulate them can be optimal for that purpose. Assuming that the two frequency bands, i.e., the RF excitation frequency band for the signal applied to the RF-DC power supply 32 and the frequency band applied to excite the transducers 44–46, are sufficiently separated, the RF power delivery can occur simultaneously with the excitation of a selected transducer 44–46 and the generation of diagnostic signals by another selected transducer 44–46. Accordingly, more RF power can be coupled into the system from the external source than in the implantable electronic circuits shown in FIGS. 1 through 3.

The control signals that are supplied to the RF decode/control section 66 via the RF coupling coil 30 can be conveyed using nearly any kind of modulation scheme, e.g., by modulating the RF excitation that powers the device, or by sending a control signal on a separate and distinct RF frequency. Also, the signals that are received from the transducer 44–46 in response to the ultrasonic wave that is propagated through the graft can be transmitted through the RF coupling coil 30 at a different frequency than the incoming excitation frequency, thereby eliminating interference between the RF-to-DC power supply 32 and data signal transmission functions.

The implantable electronic circuit shown in FIG. 4 is applicable to transit time flow measurements in which pairs of transducers 44–46 are selected for transmitting and receiving the ultrasonic wave that propagates through the one or more grafts or vessels on which the transducers 44–46 are installed. The RF decode/control section 66 can be employed to control the TX MUX 50 and the RX MUX 68 to interchange the transducers 44–46 used for transmission and reception of the ultrasonic wave on successive pulses. Using this technique, the direction of the ultrasonic wave propagation through the graft or vessel is changed on alternating pulses of ultrasonic waves, enabling transit time difference information to be gathered without requiring further multiplexer programming information to be transmitted between successive ultrasonic wave pulses. This approach greatly improves the data gathering efficiency of the implantable electronic circuit shown in FIG. 4 compared to the previously described implantable electronic circuits of FIGS. 1 through 3.

To further improve the implantable electronic circuit shown in FIG. 4 for use in sensing fluid velocity through a graft using a Doppler technique, the modification shown in FIG. 5 is made. In the latter implantable electronic circuit, a TX/RX switch 72 is added so that the implantable electronic circuit transmits and receives through the same transducer 44–46. As a result, separate transmit and receive multiplexers are not required. Instead, the MUX 38 is used to select the specific transducer 44–46 for receiving the RF excitation signal produced by the XMTR 62 so that the transducer 44–46 produces energy, e.g., an ultrasonic wave and then receives the response from fluid flowing through the graft to produce a receive data signal that is output through the RX MOD/XMTR 64. The TX/RX switch 72 prevents the signal applied by the TX AMP 58 from overdriving the input to the RX AMP 60, effectively isolating the RX AMP 60 during the time that the signal is applied to the transducer 44–46 to excite it so that it produces the desired response. However, the signal detected by the transducer 44–46 is allowed to reach the RX AMP 60 when the TX/RX switch 68 changes state (from transmit to receive). Generally, the implantable electronic circuit shown in FIG. 5 has the same benefits as described above in connection with the implantable electronic circuit shown in FIG. 4. The RF decode/control section 66 responds to the information received from outside the patient's body that determines which one of the transducers 44–46 is selected at any given time by producing an appropriate MUX control signal that is supplied to the MUX 38 over the MUX control lines 56.

In one embodiment, the RF decode/control section 66 may cause the MUX 38 to select a different transducer 44–46 for producing/receiving ultrasonic waves after a predefined number of transmit/receive cycles have elapsed. For example, a different transducer 44–46 may be selected after eight cycles have been implemented to transmit an ultrasonic wave into the graft and to receive back the echoes from the fluid flowing through the graft. By collecting data related to the status of flow through one or more grafts in this manner, it becomes unnecessary to send programming information to the RF decode/control section 66 after each cycle of transmission of the ultrasonic wave into the fluid in the graft and reception of the echo. By carrying out a predefined number of transmit/receive cycles for a given transducer 44–46 that has been selected by the MUX 38 and averaging the results, a more accurate estimate of fluid velocity through the graft or vessel can be obtained than by using only a single transmission and reception of an ultrasonic wave. Since the signal required to instruct the RF decode/control section 66 to change to the next transducer 44–46 is only required after the predefined number of cycles has been completed, the data gathering efficiency of the implantable electronic circuit is improved.

Although the transducers 44–46 that are shown in FIGS. 1 through 5 need not be ultrasonic transducers, FIG. 6 illustrates an implantable electronic circuit that is particularly applicable for use with transducers 44–46 comprising pressure sensors. Silicon pressure sensors designed to be installed on the radial artery are available from the Advanced Technologies Division of SRI of Palo Alto, Calif. For example, such pressure sensors could be disposed within the wall of a synthetic graft to sense the pressure of fluid flowing through the graft at one or more points. In response to control signals detected by the RF decode/control section 66, the MUX 38 selects a specific pressure transducer 44–46 to provide a data signal that is transmitted to the outside environment via the RF coupling coil 30. In the circuit shown in FIG. 6, a modulator/transmitter (MOD/XMTR) 70 receives the signal from the transducer 44–46 selected by the MUX 38 in response to the MUX selection signal provided over the MUX control lines 56 from the RF decode/control section 66, and, using the signal, modulates a RF signal that is supplied to the RF coupling coil 30. The RF signal transmitted by the RF coupling coil 30 thus conveys the data signal indicating pressure sensed by the selected transducer 44–46. In many cases, it will be preferable to monitor the pressure at the distal and proximal ends of a graft in order to enable the differential pressure between these ends to be determined. This differential pressure is indicative of the extent to which thromboses or other sources of lumen blockage in the graft impede fluid flowing through the lumen. In most cases, parameters such as fluid flow or velocity are better indicators of the status of flow through the graft.

RF Coupling Coil and External Coil Embodiments

FIGS. 7 through 12 illustrate details of several different embodiments for the RF coupling coil 30 that is implantable within a patient's body for receiving RF energy to provide power for the implantable electronic circuits discussed above for receiving control signals, or for transmitting data from the transducers 44–46, such as relating to the condition of flow through one or more grafts that have been installed within the patient's vascular system. Optimization of RF coupling between the implanted RF coupling coil 30 (FIGS. 1 through 6) and an external coil 90 (FIG. 7) is partially dependent upon the propagation characteristics of the human body. Since the body tissue largely comprises water, the relative dielectric constant of mammalian soft tissues is approximately equal to that of water, i.e., about 80. Also, the relative permeability of tissue comprising a body is approximately equal to one, i.e., about that of free space. The velocity of propagation of a RF signal through the body is proportional to the inverse square root of the dielectric constant and is therefore about 11% of the velocity of the signal in free space. This lower velocity reduces the wavelength of the RF signal by an equivalent factor. Accordingly, the wavelength of the RF signal transferred between the implantable RF coupling coil 30 and the external coil 90 is a design consideration when the separation distance between the two is approximately equal to or greater than one-quarter wavelength. However, at the frequencies that are of greatest interest in the present invention, one-quarter wavelength of the RF coupling signal should be substantially greater than the separation distance between the two coils.

One method for optimizing coupling between an implanted coil and a coil that is external to the body is described in *High-Efficiency Coupling-Insensitive Transcutaneous Power And Data Transmission Via An Inductive Link* by C. M. Zierhofer and E. S. Hochmair, IEEE Trans. Biomed. Eng., Vol. 37, No. 7, July 1990, pp. 716–722. This approach allows the frequency of the signal linking the implanted and external coils to vary in response to the degree of coupling between the two coils. Other methods are suitable for supplying signals to the two coils as well.

When the implantable electronic circuit includes the RF coupling coil 30 and a transducer 44–46, but does not include active electronic circuitry, the external system (e.g., external power supply and patient monitoring console 100, FIG. 8, below) senses a parameter related to the electrical input impedance of the external coil. When the external and internal coils are aligned, the inductance and the resistance of the external coil are maximized. The frequency of the signal that is used for adjusting the alignment may be different than the frequency that is used to provide electrical signals to the transducer.

The implantable electronic circuit may include an additional component to facilitate sensing of alignment between the two coils. For example, a metal disc in the implant may be detected and localized by inducing an eddy current in the disc. The external power supply and patient monitoring console may then detect the magnetic field generated by the eddy current in the disc, much as a metal detector operates. Using different frequencies for the location and therapeutic functions may avoid energy losses caused by the eddy currents.

When the implantable electronic circuitry does include active electronic circuitry, a circuit may be included with the therapeutic transducer and RF coupling coil that measures the amplitude of the signal from the external power supply and patient monitoring console that is induced in the RF coupling coil. A signal is transmitted from the implantable electronic circuitry to the external power supply and patient monitoring console, where a display provides an indication of the coupling. The operator may adjust the position of the external coil to optimize coupling between the two coils.

The penetration of RF fields in the human body has been studied extensively in conjunction with magnetic resonance imaging (MRI) systems. RF attenuation increases with frequency, but frequencies as high as 63 MHz are routinely used for whole-body imaging, although some attenuation is observed at the center of the torso at the upper end of the frequency range. In addition, MRI safety studies have also provided a basis for determining safe operating limits for the RF excitation that define the RF signal amplitude which can be safely applied without harm to the patient.

It is contemplated that for graft implants placed deep within the torso of a patient, RF excitation and frequencies used for communicating data related to the fluid flow through a graft can be up to about 40 MHz, although higher frequencies up to as much as 100 MHz may be feasible. At 40 MHz, the wavelength of the RF excitation signal in tissue is about 82 cm, which is just that point where wavelength considerations become important. For shallow implants, RF excitation at a much higher frequency may be feasible. For example, access grafts that are used for hemodialysis are typically only about 5 mm beneath the surface of the skin, in the forearm of the patient. To provide energy to the implanted electronic circuit and to receive data from transducers 44–46 associated with such grafts, frequencies in the range of a few hundred MHz may be useful. The dielectric properties of tissue have been studied to at least 10 GHz by R. Pethig, *Dielectric and Electronic Properties of Biological Materials*, Wiley Press, Chichester, 1979 (Chapter 7). Based on this study, no penetration problems are anticipated in the frequency range of interest. The relative dielectric constant of tissue decreases to about 60 at a frequency of 100 MHz and is about 50 at 1 GHz.

Figure 7:
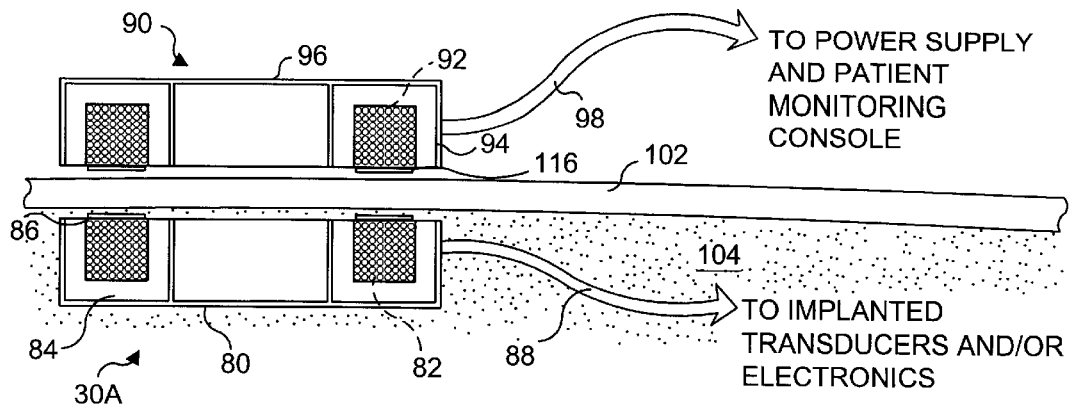
FIG. 7 shows a cross-sectional view of an implantable radio frequency (RF) coupling coil and an external coil.

In FIG. 7, a RF coupling coil 30A is shown disposed opposite the corresponding external coil 90. The RF coupling coil 30A includes a toroidal coil 82 that is wound in the hollow center channel of a toroidal shaped core 84. The core 84 and the toroidal coil 82 are contained within a biocompatible housing 80 that also provides RF shielding around the RF coupling coil 30A except where it lies opposite to the external coil 90. The external coil 90 is of similar design, including a toroidal coil 92 disposed within the hollow center portion of a toroidal shaped core 94. A housing 96 comprising a RF shield encloses much of the toroidal coil 92 and the core 94. A cable 98 conveys signals to and from an external power supply and patient monitoring console 100, which is shown in FIG. 8.

Figure 8:
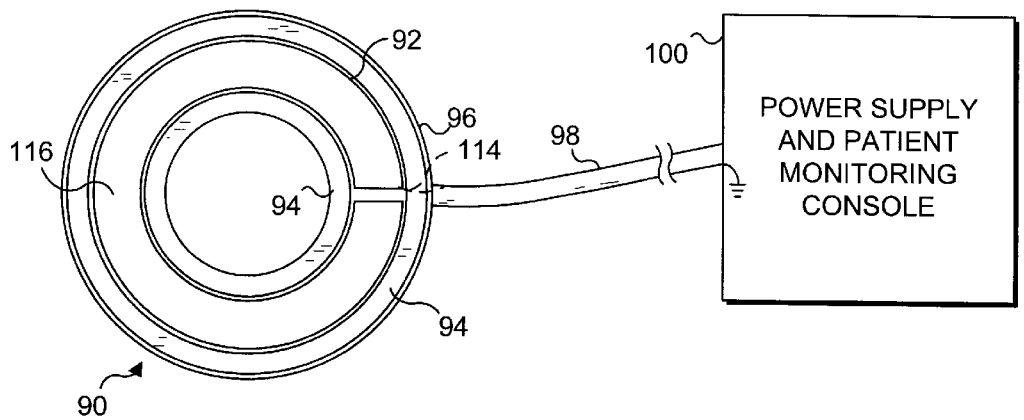
FIG. 8 shows a bottom view of the external coil shown in FIG. 7.

The external coil 90 and the RF coupling coil 30A shown in FIGS. 7 and 8 represent one embodiment used for coupling electrical energy and conveying data signals across a skin interface 102 for applications in which the RF coupling coil 30A is implanted in tissue 104 that is relatively close to the surface 102 of the skin. For example, the RF coupling coil 30A and the external coil 90 would provide the coupling required for a system used to monitor coronary artery bypass grafts (CABG). During CABG surgery, a patient's chest is opened, making it relatively straightforward to implant the RF coupling coil 30A beneath the skin as the chest is being closed at the conclusion of this surgical procedure.

Although the external core 94 and the internal core 84 need not be identical in size and shape, it is generally true that coupling will be optimal when the annular surfaces of the two cores 94 and 84 are of approximately the same dimensions and when the core halves 94 and 84 are aligned. By observing the strength of the signal transmitted from the RF coupling coil 30A, it should be possible to position the external coil 90 in proper alignment with the implanted RF coupling coil 30A so that the amplitude of the signal is maximized.

To function as a transformer core, the material used should have a relatively high magnetic permeability, at least greater than one. Although ferrite is commonly used for core materials, sintered powdered iron and other alloys can also be used. The choice of materials for the cores of the RF coupling coil 30A and the external coil 90 based on the magnetic characteristics of such materials is generally conventional.

The housing 96 on the external coil 90 provides RF shielding against electromagnetic interference (EMI). In one embodiment, the housing 96 is conductive, grounded and surrounds the external coil 90 except where the surface of the core 84 is opposite the core 94 of the implantable RF coupling coil 30A. The RF shield comprising the housing 96 also optionally includes a split annular ring 116, which is attached to the internal shield (not separately shown) at the cable 98. A similar split annular ring 86 is optionally provided on the RF coupling coil 30A covering the toroidal core 82. Split annular rings 86 and 116 are used so that a continuous loop acting as a shorted turn is avoided that would otherwise tend to attenuate coupling between the external coil 90 and the RF coupling coil 30A. The housing 80 of the implantable RF coupling coil 30A is coupled to the shield on a cable 88, and the shield is coupled to a shield on the implantable electronic circuit and the transducers 44–46. Inside the power supply and patient monitoring console 100, the shield on the cable 98 is connected to ground. The RF shields on both the external coil 90 and the implantable RF coupling coil 30A, along with the shields provided around the transducers 44–46 (described below) minimize external EMI radiation due to the use of the present invention within a patient's body, and minimize impact of electromagnetic fields in the patient's environment or the implanted electronic circuit.

Figure 9:
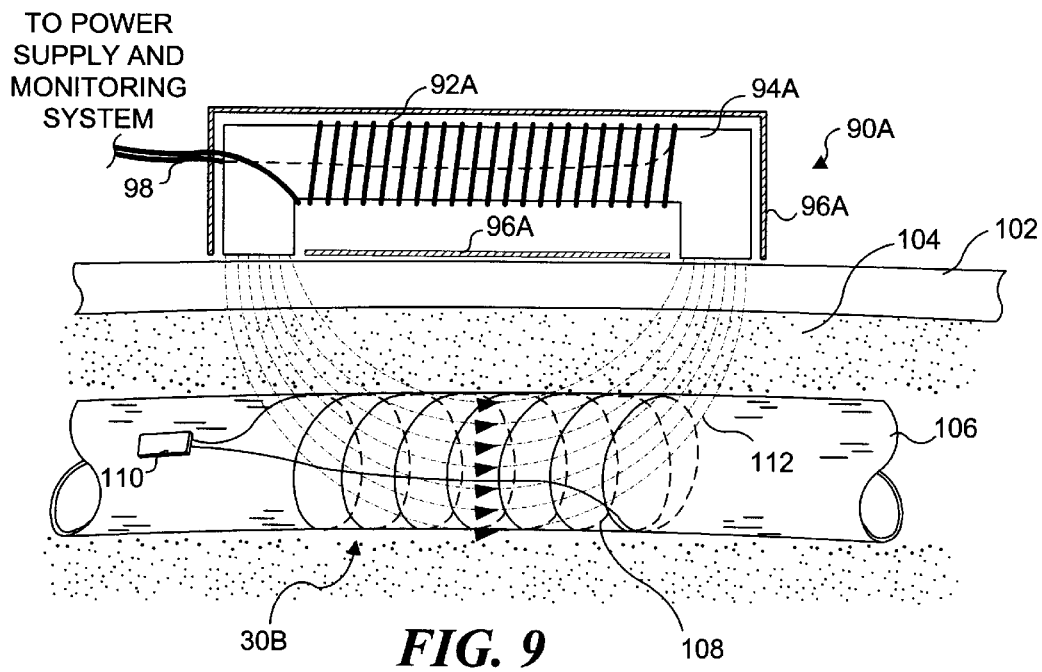
FIG. 9 shows a cut-away side elevational view of an alternative external coil and a side elevational view of a graft, showing an integrated spiral RF coupling coil within the wall of the graft.

Referring now to FIG. 9, a cylindrical RF coupling coil 30B is illustrated that comprises a plurality of spiral conductor coils 108 disposed within the wall of a graft 106. Although the drawing shows only a single layer of spiral coils 108, it is contemplated that a plurality of layers of such coils 108 may be used and that the spacing between the spiral coils 108 may be substantially closer than is illustrated in FIG. 9. The RF coupling coil 30B is coupled to an implantable electronics assembly 110 that may include any of the implantable electronic circuits shown in FIGS. 1 through 6. Not shown in FIG. 9 are the transducers 44–46 that are provided within the wall of, or on the external surface of, the graft 106.

The RF coupling coil 30B would typically be used with those grafts that are disposed relatively close to the outer surface of the patient's body, for example, within tissue 104 immediately below the dermal layer 102. In this disposition, the RF coupling coil 30B more readily couples to an external coil 90A. The external coil 90A shown in FIG. 9 has a generally C-shaped core 94A about which is coiled a plurality of turns 92A. Leads 98 pass through a housing 96A that comprises a RF shield and connect the external coil 90A to the power supply and monitoring system 100 of FIG. 8. Lines of magnetic flux 112 intersect the spiral coils 108 on the RF coupling coil 30B to provide electrical power for energizing the implantable electronic circuit 110. Similarly, the RF coupling coil 30B generates a magnetic field concentrated along the longitudinal axis of the graft 106 that is sensed by the external coil 90A to convey data indicating the flow status of the fluid through the graft 106 to the power supply and monitoring system 100 of FIG. 8.

In one embodiment, the core 94A of the external coil 90A is fabricated of a ferrite core material, or other suitable alloy. The number of coils 92A, the size of the wire, the size of the core 94A and other parameters can be determined for a particular frequency of operation using conventional transformer design criteria.

Figure 10:
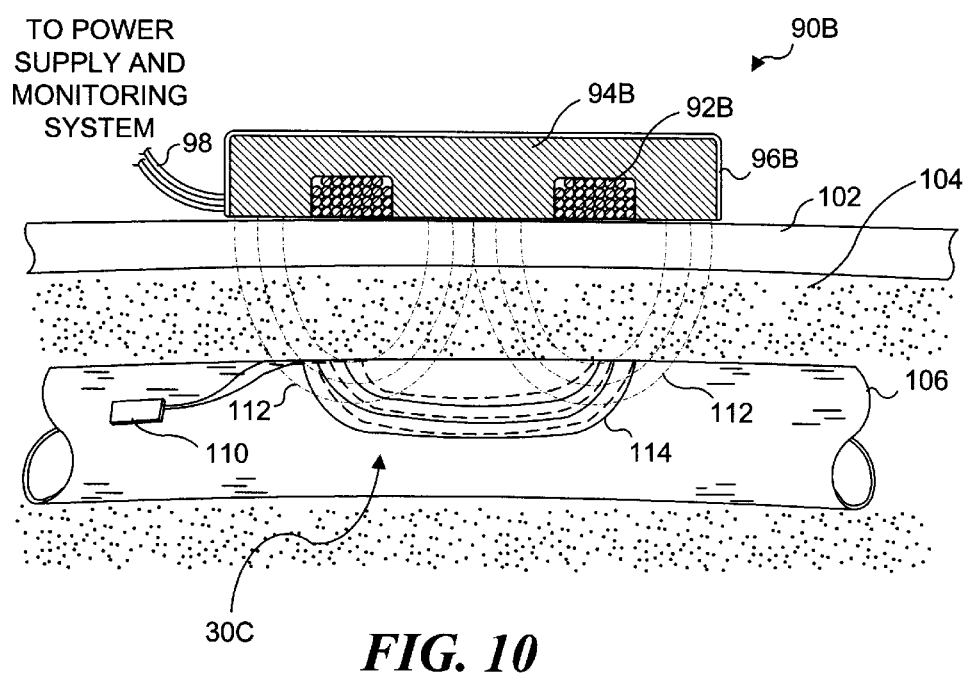
FIG. 10 shows a cut-away side elevational view of a further embodiment of an external coil and a side elevational view of a graft that includes a saddle-shaped RF coupling coil integrated within the wall of the graft.

In FIG. 10, a RF coupling coil 30C is illustrated that comprises a plurality of generally saddle shaped coils 114 disposed within the wall of the graft 106. Again, the RF coupling coil 30C is coupled to the implantable electronic circuit 110. Although only a single layer of saddle shaped coils 114 is illustrated, it is contemplated that a plurality of such interconnected layers could be provided within the wall of the graft 106.

For use with the RF coupling coil 30C, an external coil 90B is provided that includes a plurality of coils 92B wrapped around a central portion of a generally E-shaped core 94B. Leads 98 pass through a housing 96B that comprises a RF shield and connect the external coil 90B to the power supply and monitoring system 100 of FIG. 8. Lines of electromagnetic flux 112 are thus produced between the central leg and each of the end legs of the core 94B. It will therefore be apparent that this embodiment of the RF coupling coil 30C and of the external coil 90B achieve optimum coupling when the distance separating the two is minimal. Therefore, the RF coupling coil 30C and the external coil 90B are best used in applications where the graft 106 is disposed relatively close to the dermal layer 102 so that tissue 104 separating the graft 106 from the external coil 90B is only a few centimeters thick. For example, this embodiment of the RF coupling coil 30C and the external coil 90B is applicable for use with access grafts implanted just beneath the skin on the patient's forearm. Maximal coupling is achieved when longitudinal axes of the external coil 90B and the graft 106 are aligned.

Figure 11:
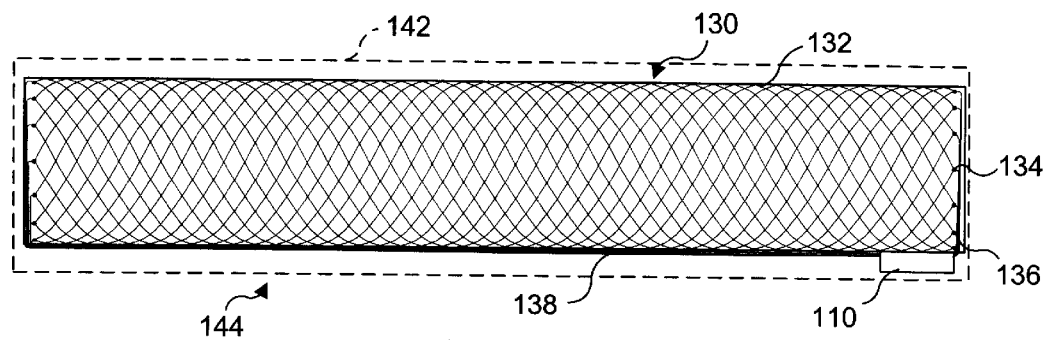
FIG. 11 shows an embodiment of a woven spiral mesh RF coupling coil that is integrally provided in a wall of a graft.

A further embodiment of a RF coupling coil 130 that is disposed within a graft 144 is shown in FIG. 11. The RF coupling coil 130 comprises a woven mesh 132 fabricated from insulated wire so that overlapping segments of the woven mesh 132 do not electrically connect in the center of the graft 144. At each end of the RF coupling coil 130, the wires comprising the woven mesh 132 are electrically coupled together at nodes 134, producing a multi-turn RF coupling coil 130. The nodes 134 are insulated from contact with body fluids or other conductors.

The couplings at the nodes 134 are preferably not made not made at random or haphazardly between the various wires comprising the woven mesh 132. A first wire comprising a helical coil having, e.g., a first orientation (which may be called a "right hand spiral") has a first end coupled to a first end of a second wire comprising a helical coil having a second orientation ("left hand spiral"; i.e., a mirror image of the right hand spiral). The voltage induced in the two wires is equal, but opposite in sign, and the two wires are thus coupled in series and provide twice the voltage between their second ends than that produced between the first and second ends of either wire alone. Accordingly, the second ends of the first two wires cannot be coupled together at the other end of the woven mesh 132 if these two wires are to contribute to the total electrical energy derived from the woven mesh 132. Rather, the wires must be "daisy chained" in series to provide one embodiment of the RF coupling coil 30C. Alternatively, a first group of wires all having a right hand spiral may all be coupled in parallel (i.e., have the ends at a first end of the woven mesh 132 coupled together, and the ends at a second end of the woven mesh 132 coupled together), with wires having a left hand spiral being similarly treated but in a second group. The groups then may be combined in series or in parallel, or subsets of the wires may be grouped and combined.

When each wire comprising the woven mesh 132 passes around the central axis of the graft through m degrees, and when there are a total of n such wires, then the equivalent number of turns in the RF coupling coil 130 is equal to n×m÷360. Leads 136 and 138 convey signals to and from nodes 134, coupling the woven mesh 132 to the implantable electronic circuit 110. A biocompatible coating 142 surrounds the wires comprising the woven mesh 132, protecting them from contact with bodily fluids.

Figure 12:
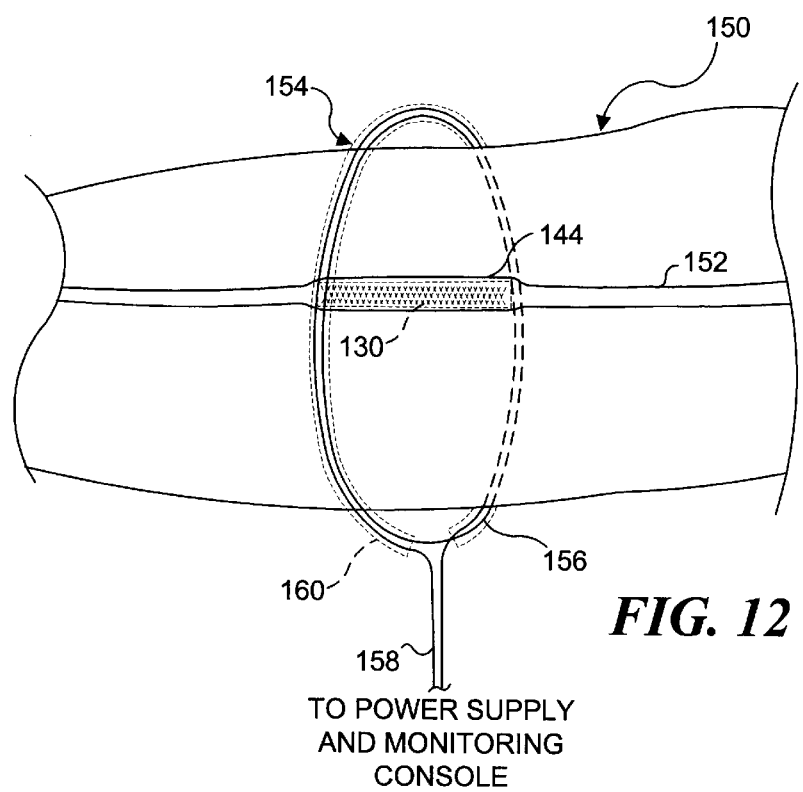
FIG. 12 shows a cut-away view of a graft implantable at a substantial depth within a patient's body, showing an external coupling coil that encompasses the portion of the patient's body in which the graft is disposed.

In those cases where grafts are implanted relatively deep inside the patient's body, at some distance from the surface of the patient's skin, an alternative external coil 154 can be employed, generally as shown in FIG. 12. In this example, an artery 152 includes a graft 144 comprising the RF coupling coil 130, which is disposed within a thigh 150 of the patient. Alternatively, the graft 144 may be implanted, for example, in the descending aorta, the iliac arteries or to provide therapy to a tumor that is deeply within the abdomen. To couple with the RF coupling coil 130, the RF coupling coil 154 includes a plurality of turns 156 sufficient in diameter to encompass the patient's thigh 150. A RF shield 160 encloses the outer extent of the RF coupling coil 154, so the RF coupling coil 154 is insensitive to capacitively coupled noise. A lead 158 couples the RF coupling coil 154 to the power supply and monitoring console 100 of FIG. 8. The RF coupling coil 154 can be made sufficiently large to encompass the portion of the body in which the implanted graft is disposed, such as the torso, another limb of the patient, or the neck of the patient. Coupling is maximized between the external coil 154 and the RF coupling coil 130 (or other RF coupling coil) used on the graft when the central axes of both the RF coupling coil 130 and the external coil 154 are coaxially aligned and when the implanted graft is generally near the center of the external coil 154. Coupling between the two coils decreases with increasing separation and begins to degrade significantly when the implanted graft 144 is more than one external coil radius away from the center point of the external coil 154. In addition, coupling is minimized when the central axes of the two coils are perpendicular.

Description of the Diagnostic Applications of Transducers

An ultrasonic transducer for monitoring flow or fluid velocity through a graft should be relatively compact if it is to be mounted adjacent a natural graft or included in the wall of a synthetic graft. Typically, an ultrasonic transducer includes an element comprising a regular solid such as a planar slab or disc of a piezoelectric material having conductive electrodes disposed on opposite sides thereof. Since such elements are relatively planar, they do not conform to the natural circular cross-sectional shape of a graft. Therefore, a graft incorporating such a transducer 44–46 that is implanted within a patient's body and which is intended to be left in place for an extended period of time requires modification of the graft or the transducer 44–46 or both.

Figure 13:
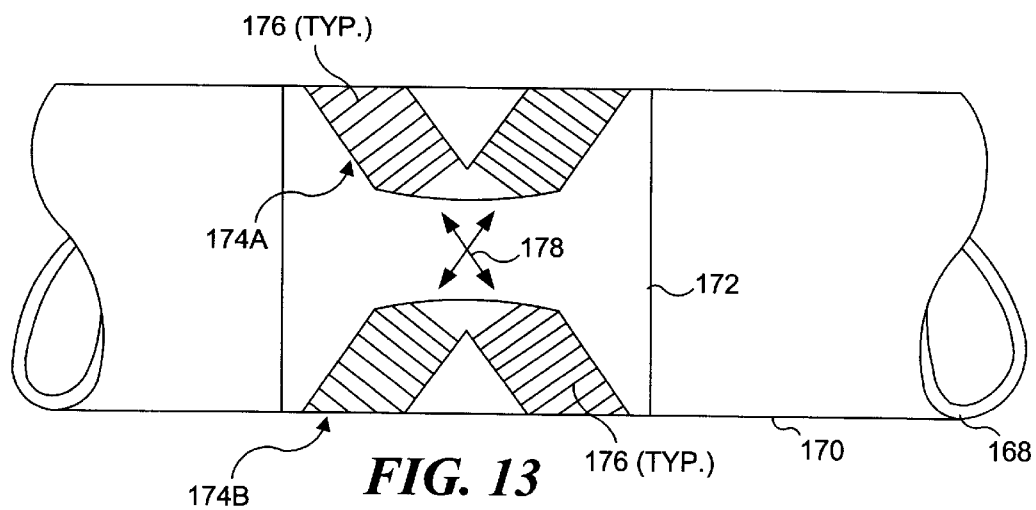
FIG. 13 shows a side elevational schematic view of a dual beam conformal transducer array on a carrier band for use around a fluid carrying vessel, in accord with the present invention.

FIG. 13 shows an embodiment of an extremely low profile ultrasonic transducer 44–46 comprising a conformal transducer array 174A disposed on opposite sides of a graft or vessel 170 from a conformal transducer array 174B. Ideally, the conformal transducer arrays 174A and 174B comprise a piezoelectric plastic used as a transduction material and having sufficient flexibility to allow the transducer elements to be wrapped around a wall 168 of the vessel 170. Such flexible piezoelectric plastic materials are readily available. It should be noted that the vessel 170 may comprise either a natural or synthetic graft, or may instead be simply a part of the patient's vascular system. However, the compact, low profile aspect of the conformal transducer array 174A makes it ideally suited for other applications outside the medical field. It is therefore contemplated that the conformal transducer array 174A, 174B shown in FIGS. 13, 14 and 15 may alternatively be used in other commercial and industrial applications in which space around the vessel wall 168 is at a premium and there is a need to monitor flow and/or velocity of a fluid through the vessel 170. Thus, the conformal transducer array 174A may be used to monitor fluid flow or velocity through a plastic or metal pipe or tube. Furthermore, it can be used for either transit time or Doppler measurements. When used for transit time measurements, as shown in FIGS. 13 and 14, the conformal transducer arrays 174A and 174B are disposed generally on opposite sides of the vessel 170 and encompass much of the circumference of the vessel 170.

However, when a pulsed Doppler measurement is made using the conformal transducer array 174A, only a single conformal transducer array 174A is required, since it first produces an ultrasonic wave that is transmitted into the vessel 170 and then receives an echo reflected back from the fluid flowing through the vessel 170. If used for continuous wave (CW) Doppler measurements, the pair of conformal transducer arrays 174A and 174B disposed on opposite sides of the vessel 170 are needed, one transducer, e.g., 174A, serving as a transmitter and the other, e.g., 174B, serving as a receiver. In each case, it is presumed that the fluid has a non-zero velocity component directed along an ultrasonic beam axis of the ultrasonic wave produced by the conformal transducer array 174A serving as a transmitter.

Figure 14:
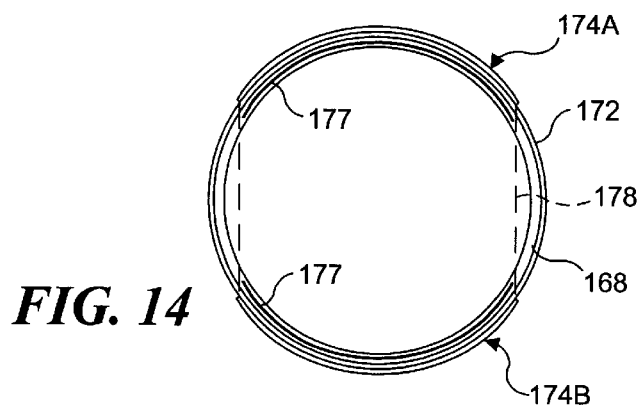
FIG. 14 shows an end elevational view of the conformal transducer array of FIG. 13, around a vessel.
Figure 15:
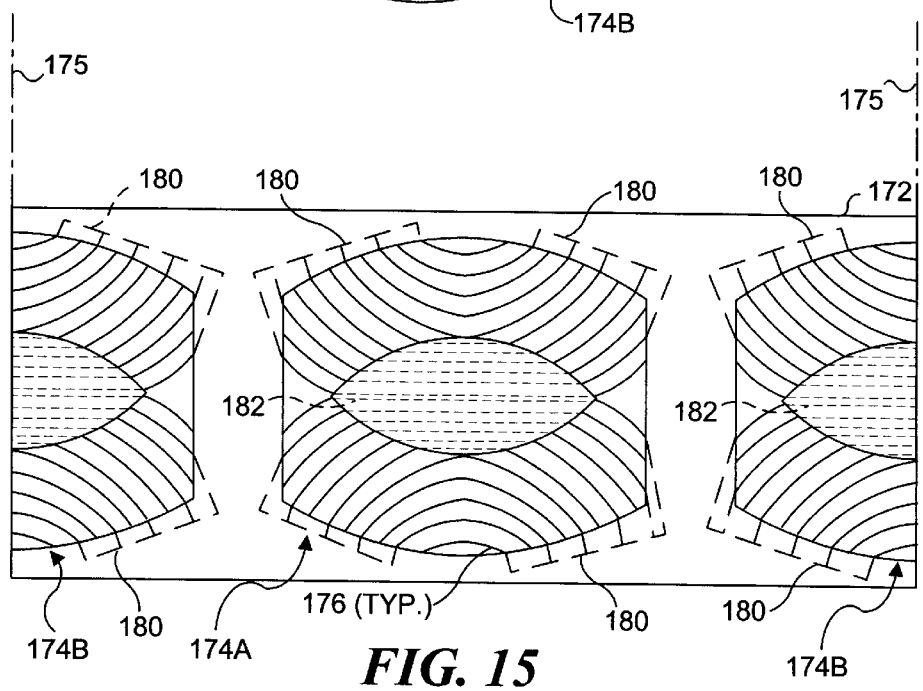
FIG. 15 shows a plan view of the conformal transducer array shown in FIGS. 13 and 14, cut along a cut line to display the dual conformal arrays in a flat disposition.

The conformal transducer arrays 174A and 174B shown in FIGS. 13 through 15 produce ultrasonic beams 178 that are tilted relative to the transverse direction across the vessel 170 in substantially equal but opposite angles with respect to the longitudinal axis of the vessel 170. Since dual beam transit time measurements are implemented by the conformal transducer arrays 174A and 174B, the results are self-compensating for tilt angle errors. This form of self-compensation is only required where the alignment of the conformal transducer arrays 174A and 174B relative to the longitudinal axis of the vessel 170 may be imperfect. For example, such imperfections are likely to occur when the conformal transducer arrays 174A and 174B are used in connection with monitoring the status of fluid flow through grafts or vascular vessels within a patient's body, since the grafts and vessels are not rigid and frequently are not straight—even within the limited length of the conformal transducer arrays 174A and 174B. For transit time measurements made on vessels 170 wherein the alignment of the conformal transducer arrays 174A and 174B relative to the longitudinal axis of the vessel 170 is well known, an opposed pair of the conformal transducer arrays 174A and 174B disposed on opposite sides of the vessel 170 is sufficient so that the added complexity of the dual beam transducer geometry is not required for self compensation.

In the case of pulsed Doppler velocity measurements, a single conformal transducer array, e.g., 174A, would again likely be adequate so long as the alignment of the conformal transducer array 174A to the vessel 170 is accurately controlled. If the alignment of the conformal transducer array 174A is not controlled or not well known, a second such conformal transducer array (not illustrated in FIGS. 13 and 14) can be used to gather velocity data along a second beam axis using pulsed Doppler velocity measurements. Assuming that the second axis is tilted in an equal but opposite direction as the first axis, the Doppler measurements made by the first 174A and second conformal transducer arrays should be self-compensating for tilt errors. In this case, the second conformal transducer array (not shown) could be mounted on the same or on an opposite side of the vessel 170 from that where the first conformal transducer array 174A is mounted to implement the Doppler measurements.

For CW or pseudo-CW Doppler velocity measurements (in which a relatively long duration pulse of ultrasonic waves is produced), the transit signal is applied for a sufficiently long period so that a second conformal transducer array is needed to receive the echo signals. In this case, a single set of diametrically opposed conformal transducer arrays 174A and 174B can be used.

As perhaps best illustrated in FIG. 14, the conformal transducer arrays 174A and 174B need not wrap entirely around the vessel 170. In the illustrated embodiment, the conformal transducer arrays 174A and 174B each span an arc of approximately 120° around the longitudinal axis of the vessel 170 (i.e., about the center of the circular vessel wall 168 as shown in FIG. 14). This geometry produces a measurement zone through which ultrasonic beams 178 propagate that is nominally equal to about 87% of the vessel outer diameter. Since the vessel wall 168 has a finite thickness, the actual measurement zone (within the lumen of the vessel wall 168) exceeds approximately 90% of the vessel internal diameter. If used for Doppler velocity measurements, it is contemplated that the conformal transducer array 174A need cover only a central portion of the vessel 170. As a result, the span of the conformal transducer array 174A can be reduced from about 120° to something within the range from about 60° to about 90°.

To produce a wide, uniform ultrasound beam such as that needed for transit time measurements of flow, the conformal transducer array 174A must produce ultrasonic waves having a wave front characterized by a substantially uniform amplitude and phase. As shown in FIG. 13, lateral projections through each of a plurality of transducer elements comprising the conformal transducer arrays 174A and 174B are indicated by straight lines 176. These straight lines indicate the centers of the transducer elements and are perpendicular to the axis of propagation of the waves 178 (represented by bidirectional arrows directed along the axes of propagation of the ultrasonic waves). In one embodiment, the spacing between the element centers, i.e., between the straight lines 176, is approximately equal to a phase angle of 90° at the transducer's excitation frequency. Thus, starting at the top of FIG. 13 and working downwardly, transducer elements disposed along each of the displayed straight lines produce acoustic waves that are successively delayed by 90°, or one-quarter wavelength in the fluid medium through which the ultrasonic waves propagate. For tissue, a sound velocity of 1,540 meters/second is normally assumed, so that the physical spacing of the projected straight lines would typically be defined by the following:

Projected Spacing in millimeters=$1.54/(4*F_0)$, where $F_0$ is equal to the center frequency in MHz. If zero degrees is assigned to the top-most element of the conformal transducer array 174A, the next element would operate at −90° relative to the top element, followed by an element operating at −180°, and then one operating at −270°, and finally by an element operating at 0° relative to the top electrode. Thus, the conformal transducer array 174A produces a succession of ultrasonic waves spaced apart by a 90° phase shift, thereby achieving a uniform phase front across the conformal transducer array 174A.

While the discussion herein is in terms of phase shifts of 90°, it will be appreciated that other types of transducer element spacings or relative displacements may require different phase shifts. For example, three phase transducers are known that employ a phase shift of 120° between adjacent elements. Additionally, physical displacements of the transducer elements in the direction of propagation of the acoustic waves may require different or additional phase shifts between the electrical signals coupled to the elements. It is possible to phase shift these signals to provide a uniform phase front in the propagating acoustic wave using conventional techniques.

Amplitude uniformity can be achieved in the ultrasonic wave front by apodizing or "shaving" the elements of the conformal array. Although shaving could be achieved in a variety of ways, in one embodiment shaving is implemented by varying the area of each element.

In one embodiment, the conformal transducer arrays 174A and 174B are carried on a band 172 made from the piezoelectric plastic material used for the element substrate, which is sized to fit snugly around an outer surface of the vessel 170. The band 172 is intended to position the conformal transducer arrays 174A and 174B in acoustic contact with the vessel wall 168. Such contact assures that the ultrasonic waves produced by the elements of the conformal transducer arrays 174A and 174B are conveyed through the vessel wall 168 and into the fluid flowing through the interior of the vessel 170. In one embodiment, the piezoelectric plastic comprising the band 172, and more particularly, the conformal transducer arrays 174A and 174B, are fabricated from a material such as polyvinylidene fluoride (PVDF), poly(vinyl cyanide-vinyl acetate) copolymer (P(VCN/VAc), or poly(vinylidene fluoride-trifluoroethylene) copolymer (P(VDF-TrFE)). In one embodiment, P(VDF-TrFE) is used because of its high piezoelectric coupling and relatively low losses.

Referring now to FIG. 15, further details of the conformal transducer arrays 174A and 174B are illustrated. In this embodiment, alternating elements of the conformal array produce ultrasonic waves differing in phase by 90°. In the view shown in FIG. 15, a cut line 175 intersects the lateral center of the conformal transducer array 174B. In practice, any cut would more likely extend through the band 172 at a point approximately midway between the conformal transducer array 174A and the conformal transducer array 174B. If the band 172 must be cut in order to wrap the band 172 around a vessel 170, i.e., when it is not possible or practical to slip the band 172 over the vessel 170 without cutting the band 172, the elements comprising the conformal transducer arrays 174A and 174B need not be interrupted or damaged. Electrodes comprising each element of the conformal transducer array 174A and 174B can be photolithographically generated on the piezoelectric plastic substrate comprising the band 172. Alternatively, the elements can be formed on a non-piezoelectric material comprising band 172, and then the material with the elements formed thereon can be bonded to a piezoelectric substrate in each area where a conformal transducer array 174A or 174B element is disposed. In this latter embodiment, it is contemplated that a flexible circuit material such as a polyimide could be employed for the band 172, and that conventional photolithographic processing methods might be used to fabricate the conformal transducer array circuitry on the band 172. Further, the centers of alternating conformal array elements are coupled together electrically via conductors 180 (shown as dashed lines) in FIG. 15. Not shown in FIGS. 13 through 15 are the leads that extend from an electronics assembly used to drive the conformal transducer arrays 174A and 174B. Any of the implantable electronic circuits shown in FIGS. 1 through 6 could be used for the electronics assembly.

The pattern of elements comprising each of the conformal transducer arrays 174A and 174B and the boundary of each conformal transducer array 174A and 174B (top and bottom as shown in FIG. 15), define sinusoidal segments. The period of the sine wave from which these sinusoidal segments are derived is approximately equal to the circumference of the band 172. Further, the amplitude of that sine wave generally depends on the desired beam angle relative to the longitudinal axis of the vessel 170. For the sinusoidal segment employed for each electrode, the amplitude is defined by:

$$\text{Amplitude} = D * \tan \Theta.$$

Similarly, the amplitude of the sinusoidal segment forming the boundary of each conformal transducer array 174A or 174B is defined by:

$$\text{Amplitude} = D / (\tan \Theta),$$

where $\Theta$ is equal to the angle between the longitudinal axis of the vessel 170 and the ultrasound beam axis and D is equal to the external diameter of the vessel 170. Accordingly, it should be apparent that one sinusoidal template could be used to draw all of the transducer elements and a second sinusoidal template (differing only in amplitude from the first) could be used to draw the boundary of each conformal transducer array 174A and 174B. The transducer elements are displaced or spaced apart from one another as required to achieve the phase relationship described above in connection with FIG. 13. In addition, the actual physical electrode pattern and placement of the elements on the band 172 can be determined by finding intersection loci between the band 172 as wrapped around the vessel 170 and equally-spaced planes. The spacing between these planes is defined by the equation noted above for the projected spacing.

Conductors 180 that each connect to adjacent transducer elements differ in phase from each other by 90°. There are two ways to achieve the 90° phase variation between the ultrasonic waves produced by successive electrodes in the conformal transducer arrays 174A and 174B. In the first approach, a uniformly poled piezoelectric plastic substrate is used and every fourth element is connected together, producing four groups of elements or electrodes that produce ultrasonic waves having phase relationships of 0°, 90°, 180° and 270°, respectively. Alternatively, a zone poled piezoelectric plastic substrate could be used and every other element can be connected together (as shown in FIG. 15). Each of these two groups is then connected to provide an in phase and a quadrature phase transceiving system, so that ultrasonic waves are produced by adjacent elements in each group have a relative phase relationship of 0° and 90°. In the first approach, a multi-layer interconnect pattern is required to connect to all traces for each of the transducer elements in the four groups. In addition, a more complex four-phase electronic driving system that includes a phase shifter is required. Specifically, the signal applied to each of the four groups must differ by 90° between successive elements to achieve the 0°, 90°, 180° and 270° driving signals. The phase shifter, e.g., may be included in the modulator that drives the conformal transducer array 174A and 174B (which may be included as a part of the RF decode section 40 of FIGS. 1 through 3 or the RF decode/control section 66 of FIGS. 4 through 6) and provides the phase shifted excitation signals applied to each successive element of the conformal transducer arrays 174A and 174B.

In the second approach, which may be preferred in some embodiments because it may simplify the electronic package required and because it may facilitate use of a simpler, double-sided electrode pattern, the piezoelectric plastic material must be locally poled in a specific direction, depending upon the desired phase of the electrode at that location. A poling direction reversal provides a 180° phase shift, eliminating the need for 180° and 270° phase-shifted signals. Thus, the zones of the substrate designated as 0° and 90° would be connected to the signal source with the elements poled in one direction, while zones for elements designated to provide a relative phase shift of 180° and 270° would be connected with the elements poled in the opposite direction. The elements producing ultrasonic waves with a relative phase relationship of 0° and 180° would comprise one group and the elements producing ultrasonic waves with a relative phase relationship of 90° and 270° would comprise a second group. Poling the different groups of elements in local regions in opposite directions is achieved by heating the material above the Curie temperature, applying electric fields of the desired polarities in each of those areas and then cooling the material below the Curie temperature while maintaining the electric fields. This occurs during manufacture of the conformal transducer arrays 174A and 174B. The final element wiring pattern required to actually energize the conformal transducer arrays 174A and 174B when they are employed for monitoring flow and/or velocity of fluid through the vessel 170 would preclude applying electric fields in opposite polarity. Accordingly, the required poling relationship would have to be realized using either temporary electrodes or by providing temporary breaks in the actual electrode pattern employed in the final conformal transducer arrays 174A and 174B.

In one embodiment, to achieve a desired frequency of operation, it is contemplated that the electrode mass would be increased to a point well beyond that required for making electrical connections. This added mass would act together with the piezoelectric plastic material to form a physically resonant system at a desired frequency. In this manner, a relatively thinner and more flexible piezoelectric plastic material can be used for the substrate comprising the band 172. Use of mass loading is conventional in the art of ultrasonic transducer design.

While the fluids within the vessel 170 may provide an effective ground plane, in one embodiment, a conductive layer 177 (FIG. 14) is included. The conductive layer 177 may be disposed on the inside of the band 172 as illustrated, the conductive layer 177 could also be placed between the conformal array transducer 174A and the band 172. In one embodiment, the conductive layer 177 is placed on the outside of the conformal array transducer 174A and the electrodes are placed on the side towards the band 172. In yet another embodiment, the conformal array transducer 174A comprises a sandwich of two layers of piezoelectric plastic, with the driven electrodes disposed between the two layers of piezoelectric plastic, and a pair of ground planes are disposed one to either outside surface of the conformal array transducer 174A. The transducer then comprises a ground plane, a layer of piezoelectric plastic, a layer of driven electrodes, a layer of piezoelectric plastic and the other ground plane. This embodiment has the advantage that the conformal array transducer 174A is well shielded. Other arrangements will also be apparent to those of skill in the art. When the conformal transducer arrays 174A and 174B are used to transmit ultrasonic waves, the conductive layer 177 may be floating (a "virtual ground") or may be coupled to a ground or common circuit (e.g., 34, FIGS. 1 through 6). When the conformal transducer arrays 174A and 174B are used to receive ultrasonic waves, the conductive layer 177 should be coupled to a common circuit or ground to reduce noise and EMI.

Figure 16:
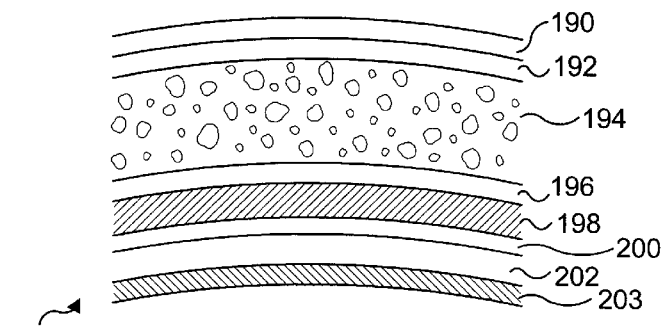
FIG. 16 shows an enlarged partial transverse cross-sectional view of the layers comprising the conformal transducer array mounted on a carrier band that is disposed around a vessel wall.

The conformal transducer arrays 174A and 174B can be formed on the band 172, but alternatively, can be included within the structure of a synthetic graft. FIG. 16 illustrates a portion of a cross-sectional view of the conformal transducer arrays 174A and 174B (not explicitly shown in FIG. 16) fabricated on the band 172. The entire transducer assembly is covered with an outer coating 190 made from a biocompatible material that serves as a barrier to protect the conformal transducer arrays 174A and 174B from bodily fluids. In one embodiment, the outer coating 190 comprises PARYLENE™ material, available from Specialty Coating Systems of Indianapolis, Ind. Outer coatings 190 comprising PARYLENE™ material may be grown to a desired thickness via vapor coating. In one embodiment, the outer coating 190 is grown to a thickness of between 0.0001" to 0.0002" (2.5 to 5 microns). Below the outer coating 190 is a RF shield 192, comprising electrically conductive flexible material or a thin foil that provides RF shielding to minimize EMI radiated from the conformal transducer arrays 174A and 174B. An acoustic backing 194 comprising a conventional syntactic foam, i.e., a polymer loaded with hollow microbubbles, also known as microspheres or microballoons, serves both for acoustic isolation and dampening and to minimize capacitive loading.

In one embodiment, the acoustic backing 194 comprises one volume of EPOTEK 377 or 301-2 epoxy glue available from Epoxy Technology of Billerica, Mass. mixed, e.g., with two or more volumes of microballoons available from PQ Corp. of Parsippany, N.J. Microballoons such as PM6545 acrylic balloons having an average diameter of 100 microns are employed in one embodiment, with the acoustic backing being 10 to 20 microballoons thick (one to two mm). The acoustic backing 194 has a relatively low dielectric constant (e.g., <10), thereby reducing capacitive loading between a rear electrode 196, a front electrode 200 and surrounding tissue. The acoustic backing 194 thus insulates the transducer elements from the surrounding fluid and tissue in a capacitive sense and also in an acoustic sense. The next layer comprises the rear electrode 196. The front electrode 200 is spaced apart from the rear electrode 196 by a piezoelectric plastic layer 198. In one embodiment, the front electrode 200 is also the conductive layer 177 of FIG. 14. As noted above, in the embodiment illustrated in FIGS. 13 through 15, the piezoelectric plastic layer 198 comprises the band 172. The piezoelectric layer 198 (or the band 172) has a relatively low dielectric constant, e.g., from about six to eight, compared to tissue (approximately 80).

In one embodiment, the rear electrode 196 and the front electrode 200 comprise multi-layer structures (although separate layers are not shown). For example, the electrodes 196 and 200 include a metallic layer, for example, titanium, that bonds well to the piezoelectric plastic material, followed by a highly conductive layer, for example, copper, followed by an oxidation resistant layer, for example, gold, and includes other metallic barrier layers, where appropriate, to prevent reaction between these layers. Such multi-layer systems are conventional and are suited for use as the electrodes 196 and 200 in the conformal transducer arrays 174A and 174B.

In one embodiment, the front electrode 200 is the "common electrode" for the transducer elements and serves as a RF shield. A front coating 202 serves as an acoustic coupling between the conformal transducer arrays 174A and 174B and the vessel 170 about which they are applied. In addition, the front coating layer 202 serves as a biocompatible layer, providing a barrier to fluid ingress into the conformal transducer arrays 174A and 174B. The transducer assembly comprising each of the layers disclosed above is wrapped around and in contact with a vessel wall 203 as shown in FIG. 16.

Figure 17:
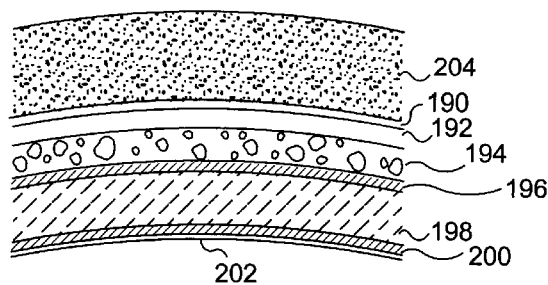
FIG. 17 shows an enlarged partial transverse cross-sectional view of the layers comprising the conformal transducer array disposed within a vessel wall of a synthetic graft.

Referring now to FIG. 17, an embodiment of the conformal transducer array fabricated as an integral component of a wall of a synthetic graft is illustrated (only a portion of a cross section showing the plurality of layers comprising the device is illustrated). A synthetic graft material 204 provides the primary structure for the synthetic graft and is adapted to be installed in a patient's vascular system. Typically, the graft material 204 comprises either a foamed fluoropolymer such as that sold by W. L. Gore Associates, Inc., or a fabric such as DACRON material. The graft material 204 is characterized by a moderate attenuation of ultrasonic signals and a structure that is somewhat porous to bodily fluids. The outer coating 190 comprising a biocompatible material that protects the transducer elements is disposed below the graft material 204. The outer coating 190 also protects other components of the transducer system from bodily fluids that may permeate the graft material 204. The RF shield 192 is disposed below the outer coating 190 to minimize transmission of EMI outside the patient's body. The acoustic backing 194 is disposed between the RF shield 192 and the rear electrode 196, and as described above, is a relatively lossy material. The piezoelectric material 198 is coupled to the rear electrode 196 and to the front electrode 200 and comprises one of the flexible piezoelectric plastics noted above. The front coating 202 is applied to the inner surface of the graft and transducer assembly and is selected for its biocompatibility, to withstand exposure to the bodily fluids flowing through the graft.

In both the conformal transducer array assembly provided in the band 172 (as shown in FIGS. 13 through 15) and the transducer assembly included within the structure of the synthetic graft wall 204, as illustrated in FIG. 17, it is contemplated that adhesive layers (not shown) may be used between the various layers. However, certain layers such as the front and rear electrodes 200 and 196 will likely need not be adhesively coupled to the piezoelectric material 198 if photolithographically formed on the piezoelectric material 198. Other layers may not require an adhesive to couple to adjacent layers, e.g., if formed of a thermoset material that self bonds to an adjacent layer when set.

Figure 18:
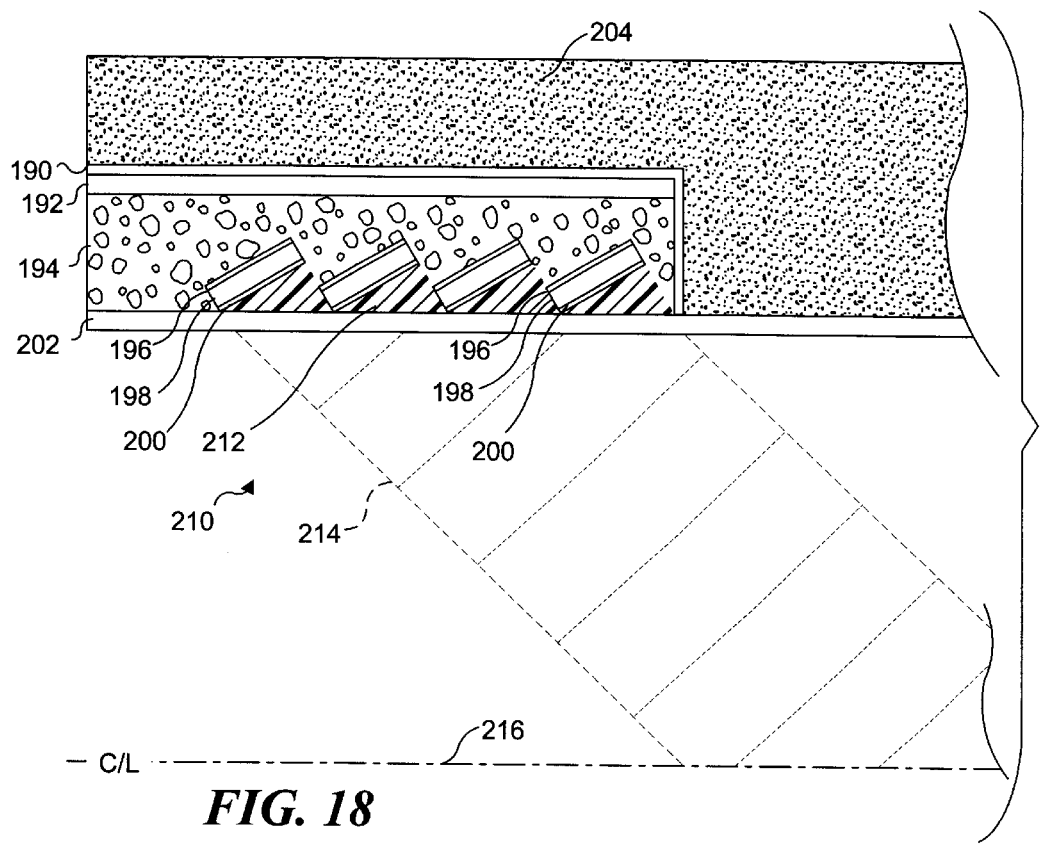
FIG. 18 shows an enlarged partial cross-sectional side view of a tilted-element transducer array disposed within a wall of a synthetic graft.

As noted above, one of the advantages of the conformal transducer array 174A or 174B is a relatively low profile. In some cases, a synthetic graft may accommodate a relatively thicker profile transducer assembly within its wall. An embodiment of a tilted element transducer 210 is illustrated in FIG. 18. Each element comprising the tilted element transducer 210 includes the rear electrode 196 and the front electrode 200 disposed on opposite sides of the piezoelectric material 198. The tilted element transducer 210 includes a plurality of elements like those shown in FIG. 18 that minimize the radial height (or thickness) of the tilted element transducer 210.

The tilted element transducer 210 is built into the wall of the synthetic graft 204, generally as shown in FIG. 18, and includes the outer coating 190, which again serves the function of providing a biocompatible layer to protect the interior portion of the graft 204 and the transducer components contained therein from exposure to bodily fluids outside the graft 204. Alternatively, the graft 204 can serve as the biocompatible coating, with the tilted element transducer disposed on the outside of the graft 204. The synthetic graft material 204, which comprises the overall structure of the graft 204, is outside the outer coating 190. The RF shield 192 extends over the tilted element transducer 210 within the protection provided by the outer coating 190. The acoustic backing 194 is disposed below the RF shield 192. The rear electrode 196 is disposed on the piezoelectric material 198 which in turn includes the front electrode 200 disposed on an opposite surface of the piezoelectric material 198.

An acoustic filler material 212 is disposed between the front electrode 200 and a front coating 202, on the interior surface of the synthetic graft 204, and is used to fill in the cavities in front of the transducer elements. The acoustic filler material 212 is characterized by a relatively low ultrasonic attenuation, so that it readily conveys the ultrasonic waves produced by the elements into the lumen of the graft 204. In order to minimize reverberations of the ultrasonic waves in this acoustic filler material 212, its acoustic impedance, which is approximately equal to sound velocity times density, is approximately equal to that of the fluid in the vessel. The velocity of sound in the acoustic filler material 212 should also be close to that of the fluid flowing through the graft 204 so that the sound beam is not significantly deflected by the acoustic filler material 212.

Alternatively, an acoustic filler material 212 having a relatively low sound velocity compared to the fluid may be used. In this case, the acoustic filler material 212 acts as an acoustic lens that deflects the sound being produced by the tilted transducer elements. For example, acoustic filler materials 212 such as silicones or fluorosilicones, typically having sound velocities about 1000 meters per second (compared to a sound velocity of approximately 1540 meters per second for blood), may be used. Low velocity lenses are conventional. The benefit of using a low velocity acoustic filler material 212 is that the tilted transducer elements can be tilted about 30% less than would be required otherwise. As a result, the overall height of the tilted element transducer 210 portion of the synthetic graft 204 can be made about 30% thinner than would be possible without the low velocity acoustic filler material 212. In combination, the plurality of tilted elements produce an ultrasonic wave 214 that propagates at an angle relative to the longitudinal axis of the synthetic graft 204, which is represented by a center line 216 in FIG. 18.

Figure 19A:
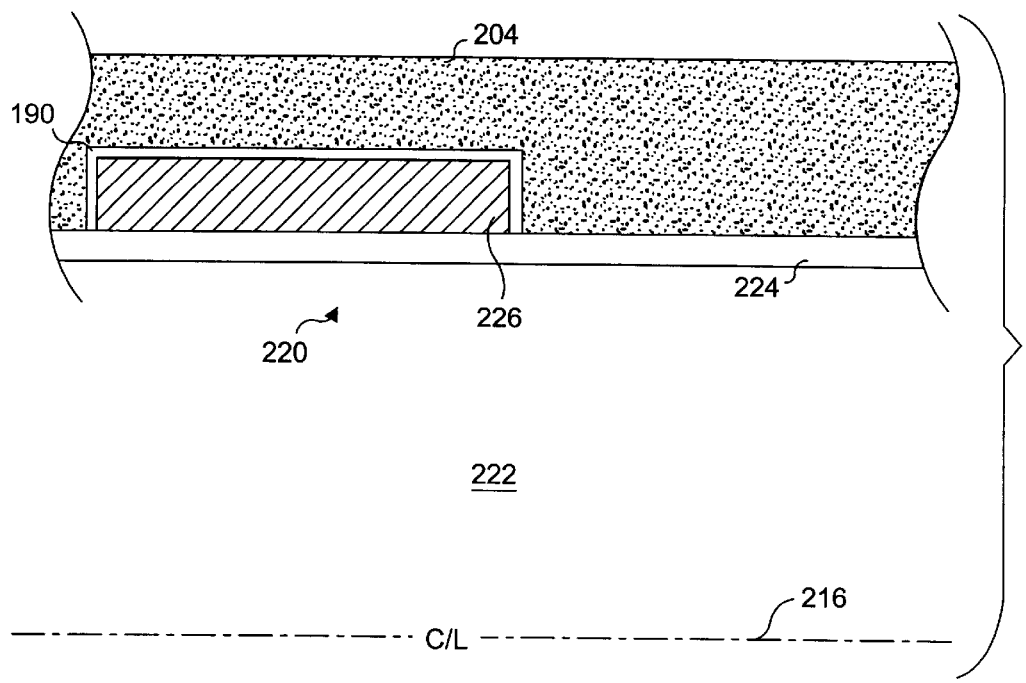
FIG. 19A shows an enlarged partial cross-sectional side view of a pressure transducer disposed within the wall of a synthetic graft.
Figure 19B:
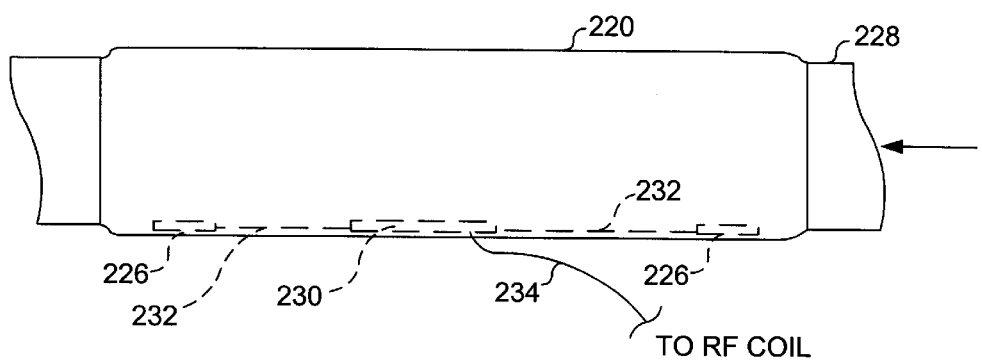
FIG. 19B shows an enlarged side elevational view of a graft in which are disposed a pair of pressure transducers.

In FIGS. 19A and 19B, an artificial graft 220 is illustrated in which pressure transducers 226 are incorporated within the wall of the graft 220 for monitoring the pressure of fluid passing through the graft 220. The outer coating 190 comprising biocompatible material is disposed between the graft material 204 and the pressure transducers 226. The outer coating 190 is employed to protect the pressure transducers 226 and other components of the transducer system from bodily fluids that may permeate the graft material 204. As shown in FIG. 19B, two pressure transducers 226 are employed, one being used for monitoring the proximal fluid pressure and the other for monitoring the distal fluid pressure. To accommodate measurements of proximal and distal fluid pressure, the pressure transducers 226 are disposed adjacent the entrance and exit ends of the artificial graft 220, respectively.

The pressure transducer 226 may comprise one of several different types of devices for sensing pressure. Such devices include an integrated circuit pressure sensor, a strain-type pressure sensor, such as a resistive strain gauge that responds to fluid pressure, etc. Various types of pressure sensing devices appropriate for incorporation in the wall of a graft are readily available from a number of different commercial sources, including SRI Center for Medical Technology of Palo Alto, Calif. Referring now to FIG. 19B, the graft 204 is illustrated coupled to a vessel 228. The pressure transducers 226 are coupled via leads 232 to an implantable electronic circuit 230, such as that illustrated in FIG. 6, as discussed above. A line 234 connects the circuit to a remotely disposed RF coupling coil (not shown in FIG. 19B) analogous to those discussed above in connection with FIGS. 7 and 8, or to one disposed within the wall of the graft, as also discussed above. The interior surface of the synthetic graft 220 includes an internal coating 224 that conveys pressure readily from the fluid flowing through an interior 222 of the artificial graft 220 to the pressure transducers 226. The inner coating 224 is biocompatible and comprises an elastomeric material.

Figure 20A:
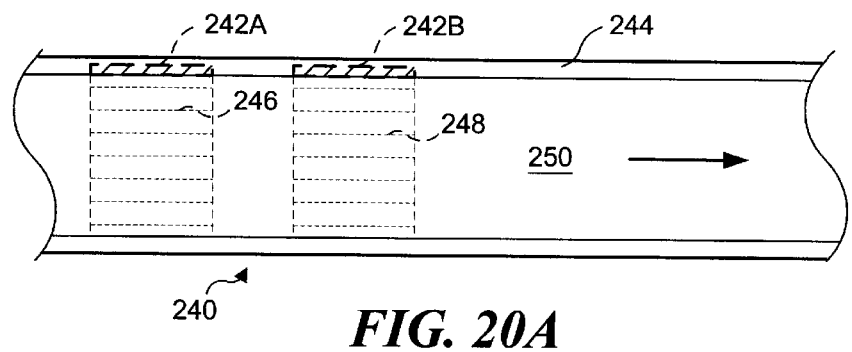
FIG. 20A shows a cross-sectional side view of a portion of a synthetic graft in which are disposed transversely oriented transducers for monitoring flow using correlation measurements.
Figure 20B:
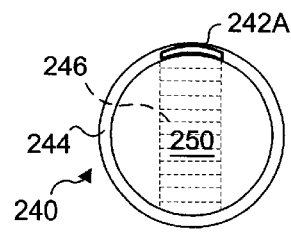
FIG. 20B shows a transverse cross-sectional view of the synthetic graft shown in FIG. 20A.

In FIGS. 20A and 20B, an alternative approach for monitoring the velocity of a fluid through an interior 250 of a synthetic graft 240 is illustrated. In this embodiment, a pair of ultrasonic transducers 242A and 242B, which may be conformal transducer arrays such as those illustrated in connection with FIGS. 13 through 15, or may be other types of ultrasonic transducers, are mounted in relatively close proximity within a wall 244 of the synthetic graft 240. Alternatively, the ultrasonic transducers 242A and 242B may be disposed externally in contact with the outer surface of a natural graft (not shown). The ultrasonic transducers 242A and 242B each produce a pulse and receive an echo back from fluid flowing through the interior 250 of the graft, the echoes being scattered from the fluid flowing therein. In this embodiment, the signal received from the ultrasonic transducer 242A in response to the echo is correlated with a similar signal from the ultrasonic transducer 242B, resulting in a time delay estimate. The velocity of the fluid is then computed by dividing a distance between the center of the ultrasonic transducer 242A and the center of the ultrasonic transducer 242B by the time delay that was determined from the correlation analysis. This is explained in more detail as follows.

The interaction of the blood with the ultrasound, even when it is moving at constant velocity, gives rise to a moving acoustic "speckle" pattern. The term speckle, as used herein, has a similar meaning in ultrasonics as in optics. It results any time that narrow band illumination is used. Optical speckle is visible when a laser (e.g., a pointer) illuminates a plain white wall. When illuminated with wideband illumination, the wall appears white and smooth. When illuminated with laser light, the wall appears to have bright and dark spots, hence the term speckle. Acoustic speckle is visible in medical ultrasound images, when the system is used to image homogeneous soft tissues such as the liver. As in optics, the acoustic speckle pattern is stationary and constant unless the tissue or flood is moving with respect to the imaging system. The same phenomenon is exploited in Doppler systems. When the echo return from moving blood is constant, there is no observable Doppler shift in the echo signal.

The blood consists of thousands of scatterers, and the ultrasound reflects from ensembles of these scatterers. The amplitude and phase of the echo, at a given range, depends on the local distribution of scatterers, which is random. The random signal of echo amplitude and phase at a given depth repeats as the blood flows past the second ultrasonic transducer 242B, if the spacing between the two ultrasonic transducers 242A and 242B is such that the ensembles of scatterers have not changed significantly, i.e., if the two ultrasonic transducers 242A and 242B are close enough to each other that turbulence has not significantly disrupted the ensembles of scatterers. Correlation of nominally identical random patterns that are displaced in time by an amount equal to the time required for the blood to move from the first beam to the second one allows the velocity to be determined when the separation between the two ultrasonic transducers 242A and 242B is known.

In other words, the first ultrasonic transducer 242A receives an echo signal that provides a speckle "image"— where the distance from the ultrasonic transducer 242A is along the vertical dimension in FIGS. 20A and 20B, and the successive echo returns are along the horizontal dimension. The two "images" from the two ultrasonic transducers 242A and 242B are correlated in the horizontal dimension, and what results is an instantaneous map of travel time vs. depth.

The sampling aperture for this system is much shorter than the time required for a heartbeat. Accordingly, a series of measurements, which may be taken during the interval between two successive heartbeats, may be processed or compared to determine peak, minimum and average blood velocity when these data are desired.

Unlike a Doppler system, the echoes in a correlation type transducer system like that shown in FIGS. 20A and 20B are not frequency shifted. Instead, the velocity signal is extracted by correlating the echo amplitude versus time signals for a pair of range bins. The velocity versus time is independently determined for each range bin, resulting in a time dependent velocity profile across the diameter of the synthetic graft 240.

Description of Therapeutic Systems

A variety of therapeutic transducers may be implanted that are responsive to and/or powered by the signals coupled into the implantable electronic circuits of FIGS. 1 through 6. One class of therapeutic transducers provide utility by enabling localized delivery or activation of specific drugs for specific purposes. One advantage to localized activation of drugs is that the side effects associated with the drugs may be reduced by only providing the drug at the site requiring treatment. This is advantageous in many situations, including chemotherapy, where the drugs are toxic.

For example, U.S. Pat. No. 5,445,608 entitled *Method And Apparatus For Providing Light-Activated Therapy*, describes a photodynamic therapy achieved by photoactivation of suitable optically active drugs. The drugs are activated via catheter-mounted light emitters inserted at the site to be treated and providing light at the wavelength required in order to activate the drugs and at the location where the activated drugs are needed for therapeutic purposes. Examples of precursor substances that can be optically activated by being broken down into drug molecules include long-chain cyanine dyes, dimers of phthalocyanine dyes and porphyrin compounds. A wide selection of solid state light sources including laser diodes and light emitting diodes is commercially available from a variety of vendors, including Motorola of Phoenix, Ariz. Laser diodes or light emitting diodes may be employed as transducers 44–46 in any of the systems shown in FIGS. 1 through 6 to provide light for photoactivation of drugs within a patient's body via signals from the implantable electronic circuit in response to signals transmitted from the power supply and patient monitoring console 100 of FIG. 8.

Similar drug activation phenomena have been reported using ultrasonic activation to break precursor substances down into drug molecules and other by-products. In this case, one or more of the transducers 44–46 of FIGS. 1 through 6 are ultrasonic transducers, several of which are described with respect to FIGS. 13 through 18. Sonochemical activation of hematoporphyrin for tumor treatment is described by S. I. Umemura et al. in *Sonodynamic Activation of Hematoporphyrin: A Potential Modality For Tumor Treatment*, published in the 1989 IEEE Ultrasonics Symposium Proceedings, IEEE cat. no. 0090-5607/89/0000-0955, pp. 955–960. Ultrasonic potentiation of adriamycin using pulsed ultrasound is described by G.H. Harrison et al. in *Effect Of Ultrasonic Exposure Time And Burst Frequency On The Enhancement Of Chemotherapy By Low-Level Ultrasound*, published in the 1992 IEEE Ultrasonics Symposium Proceedings, IEEE cat. no. 1051-0117/92/0000-1245, pp. 1245–1248. Similarly, increased toxicity of dimethlyformamide has been reported in conjunction with ultrasound by R. J. Jeffers et al. in *Enhanced Cytotoxicity Of Dimethylformamide By Ultrasound In Vitro*, published in the 1992 IEEE Ultrasonics Symposium Proceedings, IEEE cat. no. 1051-0117/92/0000-1241, pp. 1241–1244. Sonodynamic activation at one or more specific body sites to provide local drug delivery is possible when one or more of the transducers 44–46 of FIGS. 1 through 6 are designed to provide suitable ultrasonic signals and are implanted at the locations where drug activation provides therapeutic benefits. Sonodynamic effects are nonlinear effects associated with the peak compression and expansion portions of the wave cycle; at lower frequencies, the time that the peak portions of the wave have to act is greater. For this reason, lower frequencies are preferred in some embodiments. Other embodiments increase peak forces by combining two or more ultrasonic waves.

Sonodynamic activation of drug precursors may be effected via any of the transducers 174A or 174B of FIGS. 13 through 15, the piezoelectric material 198 of the graft of FIG. 17, the tilted element transducer 210 of FIG. 18 or the transducers 242A and 242B of FIGS. 20A and 20B. Sonodynamic activation may also be achieved by other transducers such as those described in connection with FIGS. 21 through 23 below.

Figure 21:
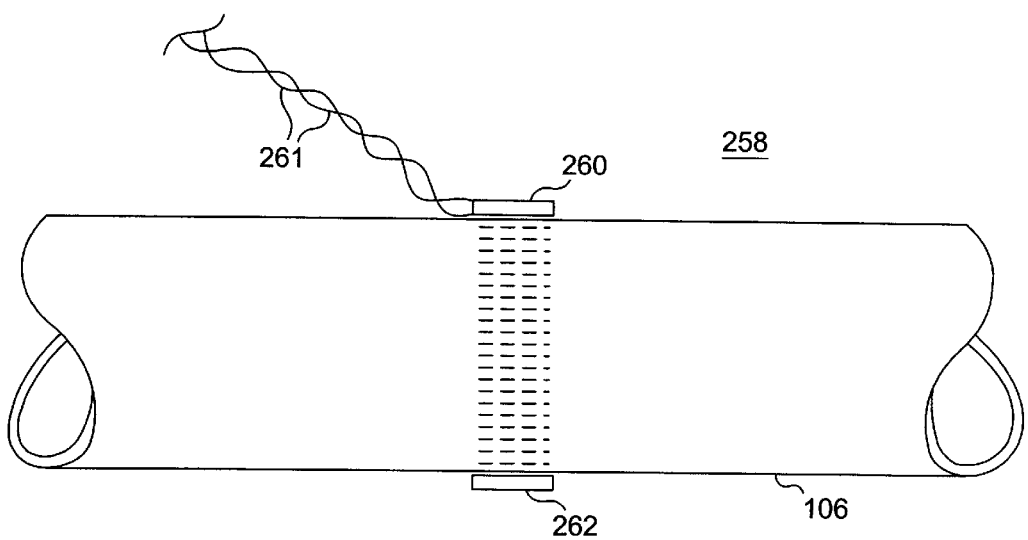
FIG. 21 illustrates an ultrasonic transducer configuration specifically designed to provide standing waves for sonochemical activation of blood-borne drug precursors.

FIG. 21 illustrates an ultrasonic transducer configuration 258 specifically designed to provide sonodynamic therapy via standing waves (shown as dashed lines). The standing waves provide sonochemical activation of bloodborne drug precursors via control signals coupled from the implantable electronic circuitry of any of FIGS. 1 through 6 by lines 261. The ultrasonic transducer configuration 258 is useful where local drug activation is desired in order to deliver the drug to either a tumor that is downstream of vessel 106 or when the downstream vasculature is the intended target for the activated drug.

The vessel 106 or graft is contacted on a first surface by an implanted ultrasonic transducer 260 and on a second surface by a device 262 that may be either another ultrasonic transducer similar to the transducer 260 or an acoustic reflector. The ultrasonic transducer 260 may be coupled to the implanted electronic assemblies using any of the approaches described in connection with FIGS. 1 through 6. In one embodiment, the layer structure described in connection with FIG. 16 is applicable to the transducer 260. The standing acoustic wave, represented by the dashed parallel lines in FIGS. 21 and 22, that is realized between the transducer 260 and the device 262 results in greater peak acoustic field strength for a given input energy level, which increases the rate of sonochemical drug activation and reduces the power levels required for sonochemical drug activation. Peak acoustic pressure increases of three- to five-fold are likely in most clinical settings.

The piezoelectric material forming the transducer 260 may comprise piezoelectric plastic materials such as PVDF, P(VCNNVAc) or P(VDF-TrFE), available from AMP Sensors of Valley Forge, Pa., or any of the piezoelectric ceramics, e.g., lead zirconium titanate. In one embodiment, PZT-4 material available from Morgan-Matroc of Bedford, Ohio provides high electroacoustic coupling and low acoustic losses. In another embodiment, the piezoelectric plastic P(VDF-TrFE) provides high electroacoustic coupling and low acoustic losses.

The transducer 260 (and, when the device 262 is a transducer, the device 262) may be of the type described, for example, with respect to FIGS. 13 through 16 or 18 and 19, or may be a slab type ultrasonic transducer similar to that shown and described in connection with FIG. 23, described below. In this application, the alignment between the transducer 260 and the device 262 must be maintained in order to preserve parallelism of the surface of transducer 260 that faces the device 262 and the surface of the device 262 that faces the transducer 260. It is also important to keep these surfaces opposed to each other, i.e., relative lateral motion of the transducer 260 and the device 262 must be inhibited. The result of maintaining this alignment is to form an acoustic cavity analogous to an optical Fabry-Perot resonator. This is achieved, in one embodiment, with the arrangement shown in FIG. 22.

Figure 22:
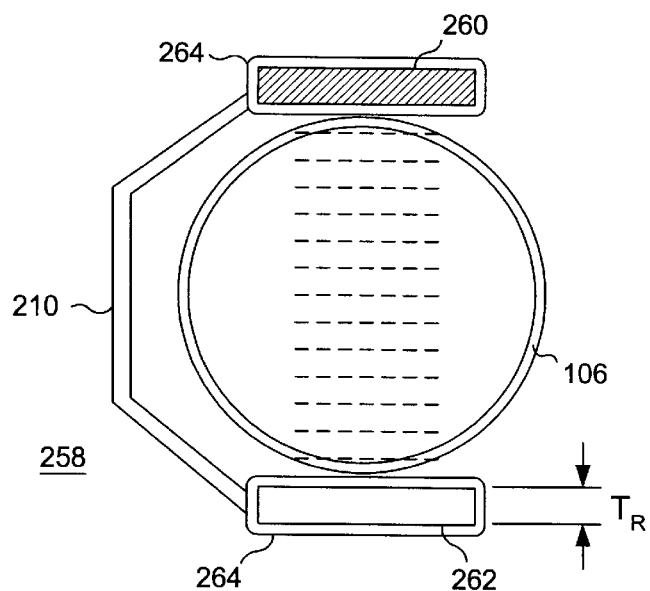
FIG. 22 shows a side view of the ultrasonic transducer configuration of FIG. 21 and illustrates a physical linkage that couples to the transducer.

FIG. 22 shows a side view of the ultrasonic transducer configuration 258 of FIG. 21 and illustrates a physical linkage 210 that couples the transducer 260 to the device 262. The physical linkage 210 is shaped to allow the wall of the vessel 106 to assume a natural curve. The physical linkage 210 also maintains the spatial relationship of the transducer 260 with the device 262, that is, maintains the acoustic emission surface of the transducer 260 in alignment with and facing the acoustically reflective surface or the acoustic emission surface of the device 262. Maintaining this alignment requires that these two surfaces be parallel to each other.

FIG. 22 also shows biocompatible coatings 264 surrounding both the transducer 260 and the device 262. The biocompatible coatings 264 are analogous to the biocompatible outer coating 190 of FIG. 16. The transducer 260 may also include an acoustic backing analogous to the acoustic backing 194 of FIG. 16, disposed on the transducer 260 as described in conjunction with FIG. 16.

When the device 262 is chosen to be an acoustic reflector, either a low impedance reflector (i.e., providing an acoustic reflection coefficient approaching −1) or a high impedance reflector (i.e., providing an acoustic reflection coefficient approaching +1) may be employed. Low-density foams (e.g., analogous to the acoustic backing material 194 of FIG. 16) or aerogels provide low acoustic impedances suitable for use in acoustic reflectors, while rigid bodies such as metals or ceramics provide high acoustic impedances suitable for use in acoustic reflectors. Setting the thickness $T_R$ of the acoustic reflector to be an odd multiple of one quarter of an acoustic wavelength, as measured in the acoustic reflector material, increases the reflection coefficient of the acoustic reflector.

Alternatively, methods for localized delivery of medication using ultrasonic activation include encapsulation of medications in delivery vehicles such as microbubbles, microspheres or microballoons, which may be ruptured to locally release the medications via localized energy provided by implanted transducers. In some embodiments, the delivery vehicles may include magnetic material, permitting the delivery vehicles to be localized via an applied magnetic field, as described in U.S. Pat. No. 4,331,654 entitled *Magnetically-Localizable, Biodegradable Lipid Microspheres*.

In one embodiment, the device 262 is formed from a magnetic ceramic or a magnetic metal alloy, and is also capable of acting as an efficient acoustic reflector. This embodiment allows localization of magnetic delivery vehicles (e.g., microbubbles, microspheres or microballoons) via the static magnetic field associated with the device 262, followed by insonification of the delivery vehicles when appropriate via ultrasound emitted by the transducer 260 in response to signals from any of the implantable electronic circuits shown in FIGS. 1 through 6. As used herein, the term "insonify" means "expose to sound" or "expose to ultrasound"; "insonification" is used to mean exposure to sound or ultrasound. Insonification of microbubbles, microballoons or microspheres can provide localized heating, can rupture them to locally release drugs or drug precursors contained in the delivery vehicles or can trigger sonodynamic activation of drug precursors that are blood-borne or that are released when the delivery vehicles rupture. Microbubbles of various compositions and filled with various drugs are developed and manufactured by ImaRx Pharmaceutical Corp. of Tucson Ariz. An advantage that is provided by use of an implanted permanent magnet for localization of magnetic delivery vehicles in this embodiment and others is that permanent magnets do not require a rechargeable energy source in order to function. In some embodiments, this can provide a way of reducing power needs from the RF-to-DC power supply 32 of FIGS. 1 through 6.

The frequency of the ultrasound from the therapeutic transducer can be varied to enhance or to reduce cavitation resulting from the ultrasound emitted from the transducer. Suppression of cavitation via frequency modulation is described in U.S. Pat. No. 5,694,936 entitled "Ultrasonic Apparatus For Thermotherapy With Variable Frequency For Suppressing Cavitation." Methods for suppression or enhancement of cavitation are described in U.S. Pat. No. 4,689,986 entitled "Variable Frequency Gas-Bubble-Manipulating Apparatus And Method." Enhancing cavitation to enhance sonodynamic activation, rupture of microspheres, microballoons or microbubbles, to locally heat tissue or to destroy tissue is possible by causing the frequency of the emitted ultrasound to decrease with time. On the other hand, cavitation may be decreased by causing the frequency of the emitted ultrasound to increase with time. This may be used to limit tissue damage while still supplying sufficient ultrasound to accomplish, e.g., a diagnostic purpose.

Sonodynamic activation of drugs or sonically-induced microbubble rupture may occur at reduced power levels when properly-phased collinear acoustic signals at two different frequencies are provided. This effect has been shown to be particularly advantageous when one signal is at a frequency that is the second harmonic of the other signal and the two signals have an appropriate phase relationship. Increased tissue damage for a given intensity of ultrasound has also been reported by S. I. Umemura in *Effect Of Second-Harmonic Phase On Producing Sonodynamic Tissue Damage*, published in the 1996 IEEE Ultrasonics Symposium Proceedings, IEEE cat. no. 0-7803-3615-1/96, pp. 1313–1318. Sonochemical activation of a gallium-deuteroporphyrin complex (ATX-70) at reduced total power density by use of properly phased signals comprising a first signal and a second signal at twice the frequency of the first signal is described by S. I. Umemura et al. in *Sonodynamic Approach To Tumor Treatment*, published in the 1992 IEEE Ultrasonics Symposium Proceedings, IEEE cat. no. 1051-0117/92/0000-1231, pp. 1231–1240. An example of a transducer that is designed to provide for transduction of two ultrasonic signals, one of which may be the second harmonic of the other, is now described with reference to FIG. 23.

Figure 23:
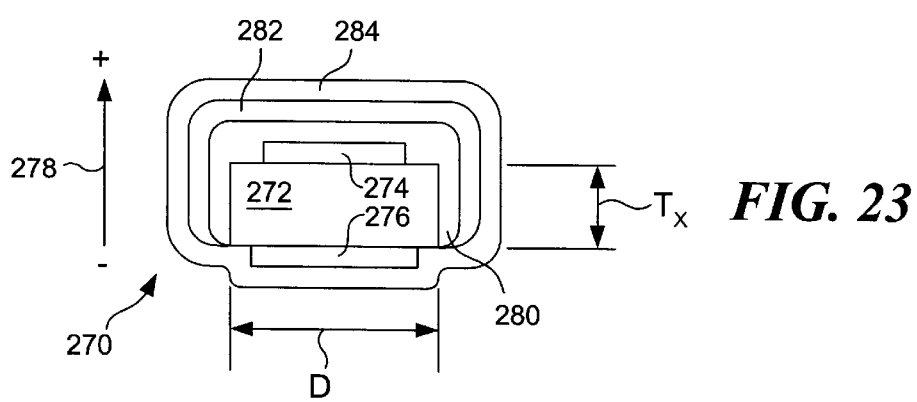
FIG. 23 illustrates a dual frequency ultrasonic transducer.

FIG. 23 illustrates an embodiment of a dual frequency ultrasonic transducer 270. The dual frequency transducer 270 is designed to provide two different frequencies of ultrasound, where one of the frequencies may be the second harmonic of the fundamental transducer frequency, when supplied with suitable electrical signals. The phases of the two signals may be adjusted by the implanted electronic circuit of FIGS. 4 through 6 and this may be in response to signals from the power supply and patient monitoring console 100 of FIG. 8. The dual frequency transducer 270 comprises a disc 272 of piezoelectric material, poled, for example, as indicated by direction arrow 278. The disc 272 has a diameter D and a thickness $T_x$. Electrode 274 and electrode 276 are formed on opposed surfaces of the disc 272 as described in conjunction with the rear and front electrodes 196 and 200 of FIG. 16 above.

In one embodiment, the diameter D is chosen to provide the desired fundamental transducer frequency via radial mode coupling while the thickness $T_x$ is chosen to provide the second harmonic of the fundamental transducer frequency via thickness mode coupling. In this case, the diameter to thickness ratio $D/T_x$ is approximately 2:1. Conventional mode charts provide more precise ratios for a variety of materials. The radial mode comprises radial particle motion primarily into and out from the center of the disc, i.e., perpendicular to the direction arrow 278, and symmetric about a cylindrical axis of the disc 272. The surfaces of the disc 272 exhibit longitudinal motion (i.e., parallel to the direction arrow 278) because of the Poisson's ratio of the material. The thickness mode comprises particle motion parallel to the direction arrow 278. As a result, acoustic energy propagating in the same direction at both frequencies may be coupled out of the disc 272 via the surfaces on which the electrodes 274 and 276 are formed. In some embodiments, the acoustic radiating surface emitting the ultrasound does not include an electrode 294 or 296. For example, electrodes may be disposed on the sidewalls, with ultrasound being emitted from the planar surfaces.

In another embodiment, the radial mode providing ultrasound at the fundamental transducer frequency may be chosen to be a harmonic of the lowest radial mode of the transducer 290. The transducer 290 may then be designed to have a larger diameter D than is possible when the lowest radial mode corresponds to the fundamental transducer frequency. This allows a larger area to be insonified by both ultrasonic signals than is otherwise feasible.

In one embodiment, frequencies of 500 kHz and 1 MHz are chosen as the two output frequencies for the dual frequency transducer 270. When the disc 272 comprises lead zirconium titanate (PZT), the diameter D is about 4 mm and the thickness $T_x$ is about 2 mm. The resulting dual frequency transducer 270 is small enough to be incorporated in an implantable device and yet also large enough to insonify a significant portion of the lumen of many blood vessels or grafts.

In an alternative embodiment, a rectangular slab may be substituted for the disc 272. In one embodiment, a lateral mode may then be used instead of the radial mode associated with the disc 272 to provide the resonance at the fundamental frequency, with the thickness mode providing the resonance at the second harmonic. Conventional mode charts are used to select the ratios of the relevant dimensions.

Coating a cylindrical sidewall of the disc 272 and one of the electrodes 274 and 276 with an acoustic absorber 280 (analogous to the acoustic backing 194 of FIG. 16) allows the other of the electrodes 274 and 276 to serve as an acoustic radiator. Choosing the acoustic absorber 280 to have a low relative dielectric constant reduces capacitive loading of the dual frequency transducer 270 by the patient's body, which, as noted above, has a high relative dielectric constant (approaching 80) and which also includes conductive solutions. Coating the acoustic absorber 280 with a grounded conductor 282, selecting the electrode 276 to be a grounded electrode and selecting the electrode 274 to be a driven electrode reduces unwanted radiation of electromagnetic signals from the transducer 272. A thin biocompatible coating 284 (analogous to the outer coating 190 of FIG. 16) protects the dual frequency transducer 270 from exposure to biological matter without preventing radiation of ultrasound from the surface bearing the electrode 276.

Other types of localized therapy include coupling a thermally-activated medication to carrier molecules that have affinity to tumor tissue. Localized heating of the tumor tissue enables selective activation of the medication in the tumor tissue, as described in U.S. Pat. No. 5,490,840 entitled *Targeted Thermal Release Of Drug-Polymer Conjugates*. Localized heating may be effected through ultrasound via an ultrasonic transducer, e.g., transducers 44–46 (FIGS. 1 through 6) implanted to allow insonification of the affected area. Higher acoustic frequencies provide shorter penetration depths, i.e., provide greater control over where the ultrasound and therefore the resultant heat is delivered. Additionally, heating is increased by ultrasonic cavitation in the presence of microbubbles, microspheres or microballoons. Other methods for providing localized magnetic forces or heating include transducers 44–46 comprising coils.

Figure 24:
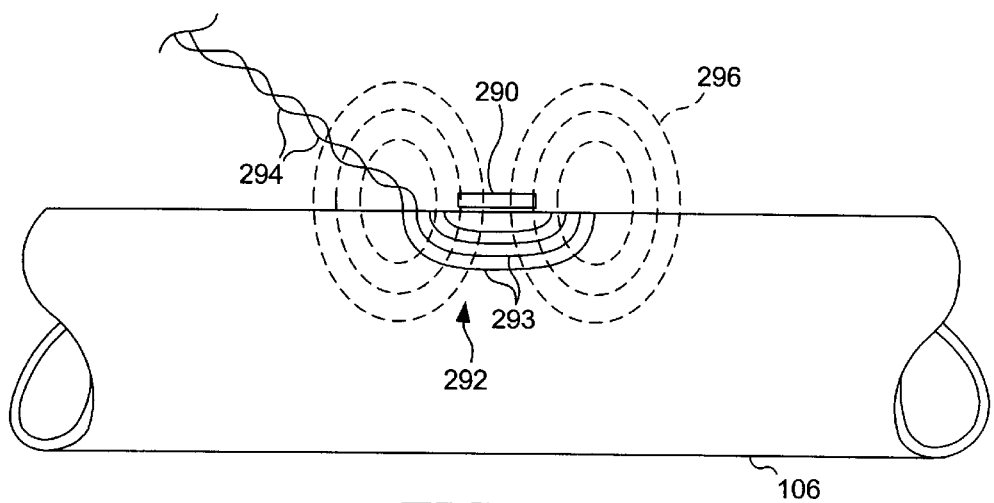
FIG. 24 illustrates an embodiment of a coil integrated into a graft.

FIG. 24 illustrates a coil 292 comprising saddle-shaped wires 293 integrated into a graft 106, either natural or artificial, that may be used to magnetically capture microbubbles, microballoons or microspheres bearing drugs. Leads 294 couple the coil 292 to the implantable electronic circuit of any of FIGS. 1 through 6. The implantable electronic circuits of FIGS. 4 through 6 may provide advantages in this situation because the frequency of the signal providing power to the implantable electronic circuits may be different from the frequency of the signals to the transducers 44–46. This may avoid a situation where the signals providing power to the implantable electronic circuits also result in release of drugs in the vicinity of the RF coupling coil 30 that is receiving the electrical power.

When a suitable current, either AC or DC, is supplied via the leads 294, a magnetic field represented by flux lines 296 is generated. The magnetic field captures magnetic delivery vehicles (e.g., microbubbles, microspheres or microballoons) that have been introduced into the patient's bloodstream. The increased concentration of delivery vehicles in the target vicinity can be used to provide local increases in delivery of drugs contained in the delivery vehicles.

Delivery vehicles including medication may be localized via a magnetic field and ruptured via an oscillating magnetic field as described in U.S. Pat. No. 4,652,257 entitled *Magnetically-Localizable, Polymerized Lipid Vesicles And Method Of Disrupting Same*. Suitable magnetic fields may be provided via application of RF or RF and DC electrical energy to the coil 292. In these embodiments, one or more of the transducers 44–46 of FIGS. 1 through 6 comprise the coil structure 292. In response to signals coupled to the implanted electronic circuit, the transducer 44–46 that is selected is activated and is supplied with current to either trap the magnetic delivery vehicles so that they can be ruptured via signals provided from another selected transducer 44–46 (e.g., an ultrasonic transducer that ruptures microbubbles via cavitation), or an oscillating magnetic field may be superposed on the magnetic fields used to trap the delivery vehicles.

Referring again to FIG. 24, in another embodiment, a permanent magnet 290 may be included with the coil 292 to provide a static magnetic field for localization of magnetic delivery vehicles. An oscillating magnetic field may then be provided via signals supplied to the coil 292 to rupture the delivery vehicles under the control of the implanted electronic circuit of any of FIGS. 1 through 6, where the coil 292 acts as one of the transducers 44–46. These embodiments may reduce power requirements for the implanted electronic circuit while retaining external control over when the drug or drug precursor is released via signals from the power supply and patient monitoring console 100 of FIG. 8. Other types of coils, e.g., analogous to coils 30B, 30C or 130 of FIGS. 9, 10 or 11, may also be used instead of the coil 292.

Figure 25:
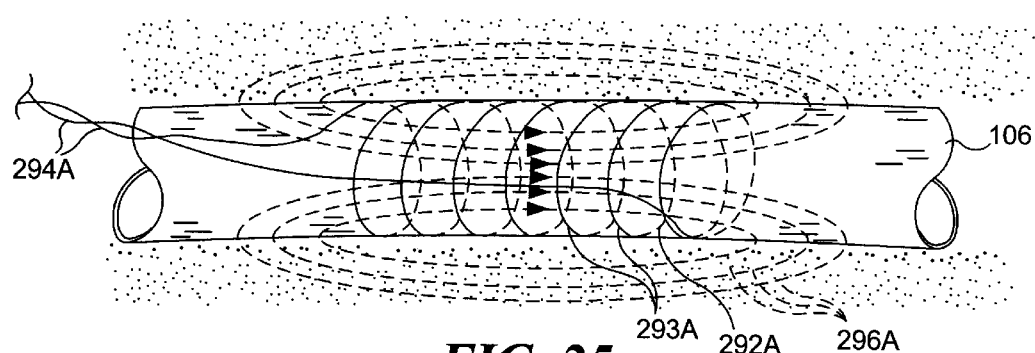
FIG. 25 illustrates another embodiment of a coil integrated into a graft.

FIG. 25 illustrates another embodiment of a coil 292A integrated into a graft. The coil 292A is analogous to the coil 292 of FIG. 24, but is shaped as a cylindrical coil rather than as a saddle-shaped spiral. Leads 294A couple wires 293A comprising the coil 292A to the implantable electronic circuit of any of FIGS. 1 through 6. When a suitable current, either AC or DC, is supplied via the leads 294A, a magnetic field represented by flux lines 296A is generated. The coil 292A may be used to captures magnetic delivery vehicles that have been introduced into the patient's bloodstream.

In another embodiment, the coils 292 or 292A may comprise a resistive material. When a current is passed through the coils 292 or 292A, a local temperature rise is produced. This local temperature rise may be employed to rupture microbubbles having a melting point slightly above normal human body temperatures. One system using microbubbles having a controlled melting point to facilitate rupture of the microbubbles at predetermined localized areas within a patient's body is described, for example, in U.S. Pat. No. 4,558,690 entitled *Method Of Administration Of Chemotherapy To Tumors*. The localized heating may be provided by a structure similar to the cylindrical RF coupling coil 30B of FIG. 9, the saddle RF coupling coil 30C of FIG. 10, the RF coupling coil 130 of FIG. 11, the coil 292 of FIG. 24 or the coil 292A of FIG. 25, with the conductors 108 or 114, the woven mesh 132 or the conductors 293 or 293A, respectively, comprising a suitably resistive material such as nichrome wire. The heating may be supplied directly by RF excitation of the coils 30B, 30C, 130, 292 or 292A or it may be effected via the implanted electronic circuits of FIGS. 1 through 6. This may be in response to signals from the power supply and patient monitoring console 100 of FIG. 8. Additionally, delivery vehicles such as microbubbles, microballoons or microspheres can increase localized heating of tissue via rupture of the delivery vehicles caused by localized application of ultrasound, as discussed, for example, in *Technical Report: Drug And Gene Delivery*, Jul. 2, 1997, ImaRx Pharmaceutical Corp.

Figure 26:
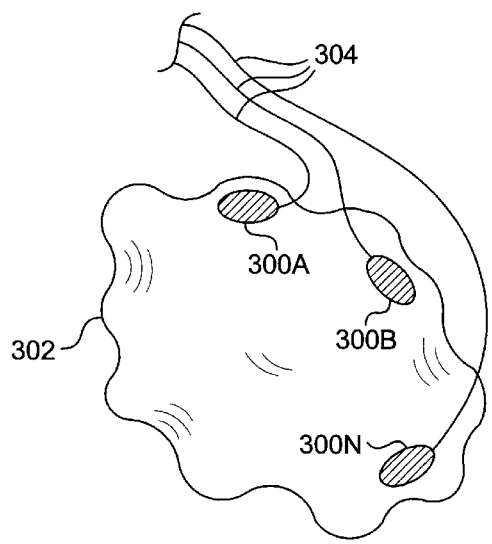
FIG. 26 illustrates a group of therapeutic transducers coupled to a tumor and controlled via an implanted electronic circuit such as that illustrated in any of FIGS. 1 through 6.

FIG. 26 illustrates a group of therapeutic transducers 300A, 300B . . . 300N coupled to a tumor 302 and controlled via an implanted electronic circuit such as that illustrated in any of FIGS. 1 through 6 via leads 304. The arrangement of FIG. 26 provides utility where the physician determines that portions of the tumor 302 are inoperable or that it is not possible to remove all of the tumor 302. Implanting therapeutic transducers 300A . . . 300N on the tumor 302 or on a blood vessel that supplies blood to the tumor 302 allows localized drug activation of blood-borne precursors. This allows chemotherapy to be provided directly to the tumor 302 without requiring high systemic levels of the chemotherapy toxin. This may be effected via ultrasonic, optical or other methods of drug activation using implantable transducers 44–46 and the implantable electronic circuitry of FIGS. 1 through 6. Alternatively, the transducers 300A . . . 300N may be employed to facilitate ultrasonic activation through drug penetration into the tumor 302 via sonophoresis, i.e., ultrasound enhancement of drug penetration into body tissues.

Methods and apparatus for localized drug delivery via sonophoresis or phonophoresis are described in U.S. Pat.

No. 4,484,569 entitled *Ultrasonic Diagnostic And Therapeutic Transducer Assembly And Method For Using*, U.S. Pat. No. 5,016,615 entitled *Local Application Of Medication With Ultrasound* and U.S. Pat. No. 5,267,985 entitled *Drug Delivery By Multiple Frequency Phonophoresis*. These patents generally discuss transdermal delivery of medication to an affected area and note that use of more than one frequency of ultrasonic energy is beneficial in some situations. These concepts become more powerful when combined with the implantable transducers 44–46 of FIGS. 4 through 6 for providing the energy to locally deliver or locally activate the medications.

The transducers 44–46 of FIGS. 1 through 6 may concentrate or activate medications by supplying heat, via resistive processes or insonification, or may employ light, magnetic fields or electrical fields for localized drug delivery or activation. The transducer 270 of FIG. 23 is also suited to increasing drug penetration of drugs into, e.g., tumors 302 via an implanted electronic circuit such as any of those shown in FIGS. 4 through 6.

Another example of an application for the systems described above occurs in the situation where a graft is implanted, for example, to correct a stenosis or to repair an aneurysm. Over time, tissue ingrowth at the ends of the graft can lead to stenosis, which can lead to thrombus formation. Thrombosis threatens the viability of the graft, and may require aggressive intervention using surgery or drugs. It is very undesirable to have to surgically resolve this situation if there is a viable alternative approach for relieving the blockage. One approach is to infuse the patient with thrombolytic drugs. This may lead to hemorrhagic consequences in other parts of the body, especially if the patient has had, for example, recent surgery. One approach to reducing the amount of thrombolytic drugs required to resolve thromboses in vitro is described in *Prototype Therapeutic Ultrasound Emitting Catheter For Accelerating Thrombolysis*, J. Ultrasound Med. 16, pp. 529–535 (1997). In this study, urokinase alone as a fibrinolytic agent was compared to urokinase in the presence of ultrasonic energy, with the latter showing marked improvement in the degree of fibrinolysis of artificial blood clots in glass tubes.

When, however, the graft includes a transducer, such as an ultrasonic transducer, coupled to the implantable electronic circuit of any of FIGS. 1 through 6, the introduction of a thrombolytic drug into the bloodstream of the patient can be followed by generation of ultrasound within the graft via the transducer and under the control of an attending physician. This allows the thrombolytic drug, e.g., urokinase, streptokinase or tissue plasminogen activator, to be activated at the site of the thrombus and under the control of the attending physician, reducing the probability of hemorrhagic consequences at portions of the patient's body remote from the site being treated. It also enables rapid onset of treatment, which can be critical in some situations, e.g., in the event of heart attack or stroke induced via thrombolysis, and may obviate invasive surgery in the event that the therapeutic transducer has already been implanted in a prior procedure.

Localized drug release via rupture of delivery vehicles such as microbubbles is one option for such drug activation. Sonodynamic or photodynamic activation of drug precursors to locally increase bioactivity is another option for such drug activation. Increased biological uptake of drugs as a result of energy provided via a transducer, for example, via acoustic streaming, cavitation, cavitation microstreaming etc., is a further option for localized drug treatment.

Additionally, when flow or pressure sensors such as are described with respect to FIGS. 13 through 15 or 18 through 20 are also included with the graft when the graft is implanted and these are also coupled to the implantable electronic circuits of any of FIGS. 2 through 6, the attending physician may be able to obtain information that is indicative of graft condition. This can allow the physician to more readily determine if the condition is treatable without resorting to invasive evaluation and intervention. Monitoring during non-invasive treatment, e.g., via local drug activation accomplished through use of an implanted blood velocity or blood pressure transducer, may allow assessment of the progress of thrombolysis that may, in turn, permit successful noninvasive treatment without incurring undue risk to the patient.

From the foregoing it will be appreciated that, although specific embodiments of the invention have been described herein for purposes of illustration, various modifications may be made without deviating from the spirit and scope of the invention. Accordingly, the invention is to be understood broadly and is not limited except as by the appended claims.

What is claimed is:

1. For subsequently altering a biological activity of a medication in a localized area of a body after the medication had been introduced intravascularly into the body, a vascular graft comprising:

a biocompatible material formed into a shape having a longitudinal axis to enclose a lumen disposed along said longitudinal axis of said shape, said lumen positioned to convey fluid through said vascular graft;

a first transducer coupled to a wall of said vascular graft; and an implantable circuit for receiving electromagnetic signals, said implantable circuit coupled to said first transducer, said first transducer configured to receive a first energy from said circuit to emit a second energy having one or more frequencies and power levels to alter said biological activity of said medication in said localized area of said body subsequent to implantation of said first transducer in said body near said localized area.

2. The vascular graft of claim 1 wherein said first transducer is selected from a group consisting of the following: an ultrasonic transducer, a plurality of light sources, an electric field transducer, an electromagnetic transducer, and a resistive heating transducer.

3. The vascular graft of claim 1 wherein said first transducer comprises a coil.

4. The vascular graft of claim 1 wherein said first transducer comprises a regular solid including piezoelectric material, and wherein a first resonance frequency, being of said one or more frequencies, is determined by a first dimension of said regular solid and a second resonance frequency, being of said one or more frequencies, is determined by a second dimension of said regular solid and further including a first electrode coupled to said regular solid and a second electrode coupled to said regular solid.

5. The vascular graft of claim 1 further comprising a second transducer coupled to said vascular graft, wherein said first and second transducers are coupled to said implantable electronic circuit and comprise ultrasonic transducers configured to provide acoustic standing waves having said one or more frequencies to alter said biological activity of said medication in a space between said first and second transducers in response to signals from said implantable electronic circuit.

6. The vascular graft of claim 1 further comprising a second transducer coupled to said vascular graft, wherein said first transducer is an ultrasonic transducer and said second transducer provides signals indicative of fluid flow through said vascular graft, said implantable circuit coupled to said second transducer.

7. The vascular graft of claim 1 wherein said implantable circuit includes a coil attached to a wall of said vascular graft and coupleable to a source of energy external to said body, to provide electrical power for energizing electrical components of said vascular graft.

8. The vascular graft of claim 7 wherein said coil is selected from a group consisting of the following: a cylindrical coil, a simple helix, a multiple helix, a woven mesh of insulated wire formed in a plurality of helices, a substantially spiral-like structure, and a saddle-shaped coil.

9. The vascular graft of claim 7 wherein said coil is generally saddle shaped and integrated into said wall, substantially conforming to a curvature of said wall about said longitudinal axis.

10. The vascular graft of claim 7 wherein said coil is adapted to electromagnetically couple to another coil that is connected to a source of energy.

11. The vascular graft of claim 1 further comprising a battery coupled to said implantable circuit.

12. For subsequently altering a biological activity of a medication in a localized area in a body after the medication had been introduced intravascularly into the body, a vascular graft comprising:

a biocompatible material formed into a shape having a longitudinal axis to enclose a lumen disposed along said longitudinal axis of said shape, said lumen positioned to convey fluid through said vascular graft;

an apparatus including a first coil, a signal source and a first control module, said first control module regulating coupling between said signal source and said first coil;

one or more diagnostic transducers sized and constructed to be implanted into said body; and an implantable device including a second coil coupled to a therapeutic transducer, said first coil being aligned with said second coil such that said signal source is configured to supply electrical power to said implantable device to energize said therapeutic transducer, said therapeutic transducer configured to emit energy, when energized, having one or more frequencies and one or more power levels to alter the biological activity of the medication in the localized area in the body subsequent to implantation of said therapeutic transducer into the body near the localized area.

13. The vascular graft of claim 12, wherein said implantable device includes a second control module coupled to said therapeutic transducer, said second control module configured to receive control signals and to activate said therapeutic transducer in response to said control signals.

14. The vascular graft of claim 13 wherein said second control module is configured to supply signals to said one or more diagnostic transducers, to receive signals from said one or more diagnostic transducers indicative of fluid flow through said vascular graft and to supply signals to said first control module describing a condition of said vascular graft based on said signals received from said one or more diagnostic transducers.

15. The vascular graft of claim 12 wherein said therapeutic transducer is an ultrasonic transducer configured to emit ultrasound to alter the biological activity of the medication by insonification.

16. For subsequently altering a biological activity of a medication after the medication had been introduced intravascularly into the body, a vascular graft comprising:

a biocompatible material formed into a shape having a longitudinal axis to enclose a lumen disposed along said longitudinal axis of said shape, said lumen positioned to convey fluid through said vascular graft;

an implantable electronic circuit including a multiplexer;

a therapeutic transducer coupled to said multiplexer, said therapeutic transducer configured to emit energy having one or more frequencies and one or more power levels to alter the biological activity of the medication in the localized area in the body subsequent to implantation of said therapeutic transducer into the body near the localized area; and a diagnostic transducer coupled to said multiplexer.

17. The vascular graft of claim 16 wherein said diagnostic transducer provides signals via said multiplexer to a RF modulator contained in said implantable electronic circuit for transmission via an implantable coil that is coupled to said implantable electronic circuit, wherein said diagnostic transducer is capable of providing signals indicative of a condition of fluid flow through said vascular graft.

18. The vascular graft of claim 17, wherein said therapeutic transducer is an ultrasonic transducer configured to emit ultrasonic energy to alter the biological activity of the medication by insonification.

19. For subsequently releasing a medication encapsulated in a delivery vehicle into a localized area of a body after the encapsulated medication had been introduced intravascularly into the body, a vascular graft comprising:

a biocompatible material formed into a shape having a longitudinal axis to enclose a lumen disposed along said longitudinal axis of said shape, said lumen positioned to convey fluid through said vascular graft;

a first transducer disposed within a wall of said vascular graft; and an implantable circuit for receiving electromagnetic signals, said implantable circuit coupled to said first transducer, said first transducer configured to receive a first energy from said implantable circuit to emit a second energy having one or more frequencies and power levels to rupture said delivery vehicle in said localized area thereby releasing said medication encapsulated in said delivery vehicle into said localized area of said body subsequent to implantation of said first transducer in said body near said localized area.

20. The vascular graft of claim 19 wherein said first transducer is selected from a group consisting of the following: an ultrasonic transducer, a plurality of light sources, an electric field transducer, an electromagnetic transducer, and a resistive heating transducer.

21. The vascular graft of claim 19 wherein said first transducer comprises a coil.

22. The vascular graft of claim 19 wherein said first transducer comprises a regular solid including piezoelectric material, and wherein a first resonance frequency, being of the one or more frequencies, is determined by a first dimension of said regular solid and a second resonance frequency, being of the one or more frequencies, is determined by a second dimension of said regular solid, and further including a first electrode coupled to said regular solid and a second electrode coupled to said regular solid.

23. The vascular graft of claim 19, further comprising a second transducer coupled to said vascular graft, wherein said first and second transducers are coupled to said implantable circuit and comprise ultrasonic transducers configured to provide acoustic standing waves having the one or more frequencies to rupture the delivery vehicle in a space between said first and second transducers in response to signals from said implantable circuit.

24. The vascular graft of claim 19, further comprising a second transducer coupled to said vascular graft, wherein said first transducer is an ultrasonic transducer and said second transducer provides signals indicative of fluid flow through said vascular graft, said implantable circuit coupled to said second transducer.

25. The vascular graft of claim 19 wherein said implantable circuit includes a coil attached to a wall of said vascular graft and coupleable to a source of energy external to said body, to provide electrical power for energizing electrical components of said vascular graft.

26. The vascular graft of claim 25 wherein said coil is selected from a group consisting of the following: a cylindrical coil, a simple helix, a multiple helix, a woven mesh of insulated wire formed in a plurality of helices, a substantially spiral-like structure, and a saddle-shaped coil.

27. The vascular graft of claim 25 wherein said coil is generally saddle shaped and integrated into said wall, substantially conforming to a curvature of said wall about said longitudinal axis.

28. The vascular graft of claim 25 wherein said coil is adapted to electromagnetically couple to another coil that is connected to a source of energy.

29. The vascular graft of claim 19 further comprising a battery coupled to said implantable circuit.

30. For subsequently releasing a medication encapsulated in a delivery vehicle into a localized area of a body after the encapsulated medication had been introduced intravascularly into the body, a vascular graft comprising:
a biocompatible material formed into a shape having a longitudinal axis to enclose a lumen disposed along said longitudinal axis of said shape, said lumen positioned to convey fluid through said vascular graft;
an apparatus including a first coil, a signal source and a first control module, said first control module regulating coupling between said signal source and said first coil;
one or more diagnostic transducers sized and constructed to be implanted into said body; and
an implantable device including a second coil coupled to a therapeutic transducer, said first coil aligned with said second coil such that said signal source is configured to supply electrical power to said implantable device to energize said therapeutic transducer, said therapeutic transducer configured to emit energy, when energized, having one or more frequencies and one or more power levels to rupture said delivery vehicle in said localized area thereby releasing said medication encapsulated in said delivery vehicle into said localized area of said body subsequent to implantation of said first transducer in said body near said localized area.

31. The vascular graft of claim 30, wherein said implantable device includes a second control module coupled to said therapeutic transducer, said second control module capable to receive control signals and to activate said therapeutic transducer in response to said control signals.

32. The vascular graft of claim 31 wherein said second control module is configured to supply signals to said one or more diagnostic transducers, to receive signals from said one or more diagnostic transducers indicative of fluid flow through said vascular graft and to supply signals to said first control module describing a condition of said vascular graft based on said signals received from said one or more diagnostic transducers.

33. The vascular graft of claim 30 wherein said therapeutic transducer is an ultrasonic transducer configured to emit ultrasonic energy to rupture said delivery vehicle.

34. For subsequently releasing a medication encapsulated in a delivery vehicle into a localized area of a body after the medication had been introduced intravascularly into the body, a vascular graft comprising:
a biocompatible material formed into a shape having a longitudinal axis to enclose a lumen disposed along said longitudinal axis of said shape, said lumen positioned to convey fluid through said vascular graft;
an implantable electronic circuit including a multiplexer; and
a therapeutic transducer coupled to said multiplexer, said therapeutic transducer configured to emit energy having one or more frequencies and one or more power levels to rupture said delivery vehicle in the localized area thereby releasing the medication encapsulated in said delivery vehicle into said localized area of said body subsequent to implantation of said therapeutic transducer in said body near said localized area.

35. The vascular graft of claim 34, further comprising a diagnostic transducer wherein said diagnostic transducer provides signals via said multiplexer to a RF modulator contained in said implantable electronic circuit for transmission via an implantable coil that is coupled to said implantable electronic circuit, wherein said diagnostic transducer is capable of providing signals indicative of a condition of fluid flow through said vascular graft.

36. The vascular graft of claim 35, wherein said therapeutic transducer is an ultrasonic transducer configured to emit ultrasonic energy to rupture said delivery vehicle.

37. For subsequently altering a biological response to a medication in a localized area of a body after the medication had been introduced intravascularly into the body, a vascular graft comprising:
a biocompatible material formed into a shape having a longitudinal axis to enclose a lumen disposed along said longitudinal axis of said shape, said lumen positioned to convey fluid through said vascular graft;
a first transducer disposed within a wall of said vascular graft; and
an implantable circuit for receiving electromagnetic signals, said implantable circuit coupled to said first transducer, said first transducer configured to receive a first energy from said implantable circuit to emit a second energy having one or more frequencies and power levels to alter said biological response to said medication of said portion of said body in said localized area of said body subsequent to implantation of said first transducer in said body near said localized area.

38. The vascular graft of claim 37 wherein said first transducer is selected from a group consisting of the following: an ultrasonic transducer, a plurality of light sources, an electric field transducer, an electromagnetic transducer, and a resistive heating transducer.

39. The vascular graft of claim 37 wherein said first transducer comprises a coil.

40. The vascular graft of claim 37 wherein said first transducer comprises a regular solid including piezoelectric material, and wherein a first resonance frequency, being of the one or more frequencies, is determined by a first dimension of said regular solid and a second resonance frequency, being of the one or more frequencies, is determined by a second dimension of said regular solid, and further including a first electrode coupled to said regular solid and a second electrode coupled to said regular solid.

41. The vascular graft of claim 37 further comprising a second transducer coupled to said vascular graft, wherein said first and second transducers are coupled to said implantable circuit and comprise ultrasonic transducers configured to provide acoustic standing waves having the one or more frequencies to alter said biological activity in a space between said first and second transducers in response to signals from said implantable circuit.

42. The vascular graft of claim 37, further comprising a second transducer coupled to said vascular graft, wherein said first transducer is an ultrasonic transducer and said second transducer provides signals indicative of fluid flow through said vascular graft, said implantable circuit coupled to said second transducer.

43. The vascular graft of claim 37 wherein said implantable circuit includes a coil attached to a wall of said vascular graft and coupleable to a source of energy external to said body, to provide electrical power for energizing electrical components of said vascular graft.

44. The vascular graft of claim 43 wherein said coil is selected from a group consisting of the following: a cylindrical coil, a simple helix, a multiple helix, a woven mesh of insulated wire formed in a plurality of helices, a substantially spiral-like structure, and a saddle-shaped coil.

45. The vascular graft of claim 43 wherein said coil is generally saddle shaped and integrated into said wall, substantially conforming to a curvature of said wall about said longitudinal axis.

46. The vascular graft of claim 43 wherein said coil is adapted to electromagnetically couple to another coil that is connected to a source of energy.

47. The vascular graft of claim 37 further comprising a battery coupled to said implantable circuit.

48. For subsequently altering a biological response to a medication in a localized area of a body after the medication had been introduced intravascularly into the body, a vascular graft comprising:
   a biocompatible material formed into a shape having a longitudinal axis to enclose a lumen disposed along said longitudinal axis of said shape, said lumen positioned to convey fluid through said vascular graft;
   an apparatus including a first coil, a signal source and a first control module, said first control module regulating coupling between said signal source and said first coil;
   one or more diagnostic transducers coupled to a vascular graft sized and constructed to be implanted into said body; and
   an implantable device including a second coil coupled to a therapeutic transducer said first coil being aligned with said second coil such that said signal source is configured to supply electrical power to said implantable device to energize said therapeutic transducer, said therapeutic transducer configured to emit energy, when energized, having one or more frequencies and one or more power levels to alter said biological response to said medication of said portion of said body in said localized area in said body subsequent to implantation of said therapeutic transducer in said body near said localized area.

49. The vascular graft of claim 48, wherein said implantable device includes a second control module coupled to said therapeutic transducer, said second control module capable to receive control signals and to activate said therapeutic transducer in response to said control signals.

50. The vascular graft of claim 49 wherein said second control module is configured to supply signals to said one or more diagnostic transducers, to receive signals from said one or more diagnostic transducers indicative of fluid flow through said vascular graft and to supply signals to said first control module describing a condition of said vascular graft based on said signals received from said one or more diagnostic transducers.

51. The vascular graft of claim 48 wherein said therapeutic transducer is an ultrasonic transducer configured to emit ultrasonic energy to alter said biological response to said medication.

52. For altering a biological response to a medication of a portion of a body in a localized area of said body, a vascular graft comprising:
   a biocompatible material formed into a shape having a longitudinal axis to enclose a lumen disposed along said longitudinal axis of said shape, said lumen positioned to convey fluid through said vascular graft;
   an implantable electronic circuit including a multiplexer;
   a therapeutic transducer coupled to said multiplexer, said therapeutic transducer configured to emit energy having one or more frequencies and one or more power levels to alter said biological response to said medication of said portion of said body in said localized area of said body subsequent to implantation of said therapeutic transducer into said body near said localized area;
   a diagnostic transducer coupled to said multiplexer; and
   a vascular graft coupled to said diagnostic transducer.

53. The vascular graft of claim 52 wherein said diagnostic transducer provides signals via said multiplexer to a RF modulator contained in said implantable electronic circuit for transmission via an implantable coil that is coupled to said implantable electronic circuit, wherein said diagnostic transducer is capable of providing signals indicative of a condition of fluid flow through said vascular graft.

54. The vascular graft of claim 53, wherein said therapeutic transducer is an ultrasonic transducer configured to emit ultrasonic energy to alter said biological response to said medication of said portion of said body.

55. A vascular graft comprising:
   a biocompatible material formed into a shape having a longitudinal axis to enclose a lumen disposed along said longitudinal axis of said shape, said lumen positioned to convey fluid through said vascular graft;
   a first transducer coupled to a wall of said vascular graft; and
   an implantable circuit for receiving electromagnetic signals, said implantable circuit coupled to said first transducer, said first transducer configured to receive a first energy from said circuit to emit a second energy having one or more frequencies and power levels to subsequently alter a biological activity of a medication in a localized area of a body after the medication had been introduced intravascularly into said body, subsequent to implantation of said first transducer in said body near said localized area.

56. A vascular graft comprising:
a biocompatible material formed into a shape having a longitudinal axis to enclose a lumen disposed along said longitudinal axis of said shape, said lumen positioned to convey fluid through said vascular graft;
a first transducer disposed within a wall of said vascular graft; and
an implantable circuit for receiving electromagnetic signals, said implantable circuit coupled to said first transducer, said first transducer configured to receive a first energy from said implantable circuit to emit a second energy having one or more frequencies and power levels to subsequently rupture a delivery vehicle containing an encapsulated medication in a localized area of a body after the encapsulated medication had been introduced intravascularly into said body, to release said encapsulated medication into said localized area of said body, subsequent to implantation of said first transducer in said body near said localized area.

* * * * *